(12) United States Patent
Jones et al.

(10) Patent No.: US 10,345,480 B2
(45) Date of Patent: Jul. 9, 2019

(54) MID-INFRARED ACID SENSOR

(71) Applicant: SCHLUMBERGER TECHNOLOGY CORPORATION, Sugar Land, TX (US)

(72) Inventors: Timothy Jones, Cambridge (GB); Nathan Lawrence, Cambridge (GB); Go Fujisawa, Sagamihara (JP); Sheng Chao, Cambridge (GB); Li Jiang, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/511,336

(22) PCT Filed: Sep. 9, 2015

(86) PCT No.: PCT/US2015/049068
§ 371 (c)(1),
(2) Date: Mar. 15, 2017

(87) PCT Pub. No.: WO2016/044010
PCT Pub. Date: Mar. 24, 2016

(65) Prior Publication Data
US 2018/0231684 A1 Aug. 16, 2018

(30) Foreign Application Priority Data
Sep. 15, 2014 (GB) .................................. 1416264.8

(51) Int. Cl.
*G01V 8/14* (2006.01)
*G01N 21/3577* (2014.01)
(Continued)

(52) U.S. Cl.
CPC ................ *G01V 8/14* (2013.01); *E21B 49/08* (2013.01); *G01N 21/15* (2013.01);
(Continued)

(58) Field of Classification Search
CPC ........... G01V 8/14; E21B 49/08; G01N 21/15
See application file for complete search history.

(56) References Cited

U.S. PATENT DOCUMENTS

| 4,922,714 A | 5/1990 | Grob et al. |
| 5,049,742 A | 9/1991 | Hosonuma et al. |

(Continued)

FOREIGN PATENT DOCUMENTS

| CN | 101893558 A | 11/2010 |
| DE | 10255769 A1 | 6/2004 |

(Continued)

OTHER PUBLICATIONS

Hawkins, G. et al., "Cooled infrared filters and dichroics for the sea and land surface temperature radiometer", Applied Optics, 2013, 52(10), pp. 2125-2135.

(Continued)

*Primary Examiner* — Hugh Maupin

(57) ABSTRACT

A sensor is provided for monitoring a mineral acid dissolved in a liquid. The sensor includes an internal reflection window which, in use, is in direct contact with the liquid. The sensor further includes a mid-infrared light source which directs a beam of mid-infrared radiation into said window for attenuated internal reflection at an interface between the window and the liquid. The sensor further includes a first narrow bandpass filter which preferentially transmits mid-infrared radiation over a band of wavelengths corresponding to an absorbance peak of the dissolved mineral acid to filter internally reflected mid-infrared radiation received from the window. The sensor further includes an infrared detector (Continued)

which detects filtered mid-infrared radiation transmitted through the first filter. The sensor further includes a processor arrangement, operably coupled to the infrared detector, which measures the intensity of the detected mid-infrared radiation transmitted through the first filter, and determines therefrom an amount of the mineral acid dissolved in the liquid.

20 Claims, 12 Drawing Sheets

(51) Int. Cl.
    *G01N 21/552*     (2014.01)
    *E21B 49/08*     (2006.01)
    *G01N 21/15*     (2006.01)
    *G01N 21/3504*     (2014.01)
    *G01N 33/00*     (2006.01)

(52) U.S. Cl.
    CPC ..... *G01N 21/3504* (2013.01); *G01N 21/3577* (2013.01); *G01N 21/552* (2013.01); *G01N 33/004* (2013.01); *E21B 2049/085* (2013.01); *G01N 2021/154* (2013.01); *G01N 2201/0696* (2013.01); *G01N 2201/12* (2013.01); *Y02A 50/244* (2018.01)

(56) References Cited

U.S. PATENT DOCUMENTS

| | | | |
|---|---|---|---|
| 5,859,430 | A | 1/1999 | Mullins et al. |
| 6,147,762 | A | 11/2000 | Haschberger et al. |
| 6,215,592 | B1 | 4/2001 | Pelekhaty |
| 6,343,167 | B1 | 1/2002 | Scalora et al. |
| 6,507,396 | B1 | 1/2003 | Godfried et al. |
| 6,627,873 | B2 | 9/2003 | Tchakarov et al. |
| 6,958,818 | B1 | 10/2005 | Payne |
| 6,995,360 | B2 | 2/2006 | Jones et al. |
| 7,123,416 | B1 | 10/2006 | Erdogan et al. |
| 7,407,566 | B2 | 8/2008 | Jiang et al. |
| 7,697,141 | B2 | 4/2010 | Jones et al. |
| 7,804,598 | B2 | 9/2010 | Hall et al. |
| 9,013,702 | B2 | 4/2015 | Freese |
| 2003/0062472 | A1 | 4/2003 | Mullins et al. |
| 2003/0147159 | A1* | 8/2003 | Dube ............... B08B 7/0035 359/833 |
| 2005/0269499 | A1 | 12/2005 | Jones et al. |
| 2006/0097203 | A1 | 5/2006 | Bykanov et al. |
| 2006/0139646 | A1 | 6/2006 | DiFoggio |
| 2006/0175547 | A1 | 8/2006 | DiFoggio et al. |
| 2006/0177939 | A1* | 8/2006 | Lehmann ............... G01J 3/42 436/164 |
| 2008/0165356 | A1 | 7/2008 | DiFoggio et al. |
| 2008/0173805 | A1 | 7/2008 | Indo et al. |
| 2010/0195105 | A1 | 8/2010 | Myrick et al. |
| 2011/0228279 | A1 | 9/2011 | Lucey |
| 2012/0025103 | A1 | 2/2012 | Deshmukh et al. |
| 2012/0170023 | A1* | 7/2012 | Szobota ............. G01N 21/3577 356/51 |
| 2012/0290208 | A1 | 11/2012 | Jiang et al. |
| 2013/0056626 | A1 | 3/2013 | Shen et al. |
| 2013/0070231 | A1 | 3/2013 | Nauka et al. |
| 2013/0284900 | A1 | 10/2013 | Freese et al. |
| 2014/0076551 | A1 | 3/2014 | Pelletier et al. |
| 2015/0114631 | A1* | 4/2015 | Chen ............... E21B 47/065 166/250.15 |
| 2016/0139296 | A1* | 5/2016 | Perkins ............. E21B 47/102 356/416 |
| 2017/0241899 | A1 | 8/2017 | Jones et al. |
| 2017/0242149 | A1 | 8/2017 | Fujisawa et al. |
| 2017/0242150 | A1 | 8/2017 | Jones et al. |

FOREIGN PATENT DOCUMENTS

| | | |
|---|---|---|
| DE | 102010045643 A1 | 3/2012 |
| EP | 0795744 A1 | 9/1997 |
| EP | 1967872 A1 | 9/2008 |
| GB | 2345753 A | 7/2000 |
| GB | 2395553 A | 5/2004 |
| GB | 2402476 A | 12/2004 |
| GB | 2507959 A | 5/2014 |
| JP | S5831307 A | 2/1983 |
| JP | 2013054368 A | 3/2013 |
| KR | 20120075182 A | 7/2012 |
| WO | WO0140771 A2 | 6/2001 |
| WO | WO2006063094 A1 | 6/2006 |
| WO | WO2009000490 A1 | 12/2008 |
| WO | WO2012073791 A1 | 6/2012 |
| WO | WO2016044008 A1 | 3/2016 |
| WO | WO2016048655 A1 | 3/2016 |

OTHER PUBLICATIONS

Baker, M. L. et al., "Effects of the Variation of Angle of Incidence and Temperature on Infrared Filter Characteristics", Applied Optics, 1967, 6(8), pp. 1343-1351.

Belyaeva, A. I., "Cryogenic infrared multilayer filters: the origin of low temperature shift in the pass-band edge", Proceedings of SPIE, 1999, 3890, pp. 87-92.

Blifford, I. H., "Factors Affecting the Performance of Commercial Interference Filters", Applied Optics, 1966, 5(1), pp. 105-111.

Born, M. et al., "Principles of Optics", pp. 323-333, 6th edition, Pergamon Press, Oxford (1980).

Chen, T-C. et al., "Influences of Temperature and Stress on Transmission Characteristics of Multilayer Thin-Film Narrow Bandpass Filters", Japanese Journal of Applied Physics, Part 1, 40(6A), pp. 4087-4096.

Evans, C. S. et al., "Filters for v2 band of CO2: monitoring and control of layer deposition", Applied Optics, 1976, 15(11), pp. 2736-2745.

Harrick, N. J., "Internal Reflection Spectroscopy", Wiley Interscience, New York, New York, USA, 1967, pp. 43-44.

Heath, D. F., et al., "Characterization of a "hardened" ultrastable UV linear variable filter and recent results on the radiometric stability of narrow band interference filters subjected to temperature/humidity, thermal/vacuum and ionizing radiation environments", SPIE, 1998, 3501, pp. 401-411.

Kaplan, S. G. et al., "Characterization of narrowband infrared interference filters", Proceeding of SPIE, 1998, 3425, 48-55.

Kim, S-H. et al., "Temperature Dependence of Transmission Center Wavelength of Narrow Bandpass Filters Prepared by Plasma Ion-Assisted Deposition", Journal of Korean Physical Society, 2004, 45(1), pp. 93-98.

Li, B. et al., "Improving low-temperature performance of infrared thin-film interference filters utilizing the intrinsic properties of IV-VI narrow-gap semiconductors", Optics Express, 2004, 12(3), pp. 401-404.

Li, B. et al., "Recent progress in improving low-temperature stability of infrared thin-film interference filters", Optics Express, 2005, 13(17), pp. 6376-6380.

Macleod, H. A., "Production Methods and Thin-Film Materials" in Thin-Film Optical Filters, 4th edition, pp. 489-568, CRC Press, Boca Raton, Florida (2010).

Mansuno, K. et al., "Enhanced Contrast of Wavelength-Selective Mid-Infrared Detectors Stable Against Incident Angle and Temperature Changes", Japanese Journal of Applied Physics, 2011, 50(3R), pp. 037201 (7 pages).

Piccioli, N. et al., "Optical Constants and Band Gap of PbTe from Thin Film Studies Between 25 and 300 K", Journal of Physics Chemical Solids, 1974, 35, pp. 971-977.

Ritter, E. et al., "Influence of Substrate Temperature on the Condensation of Vacuum Evaporated Films of MgF2 and ZnS", Journal of Vacuum Science and Technology, 1969, 6, pp. 733-736.

(56) References Cited

OTHER PUBLICATIONS

Sakaguchi, S., "Temperature Dependence of Transmission Characteristics of Multilayer Film Narrow Bandpass Filters", Japanese Journal of Applied Physics, 1999, 38, pp 6362-6368.
Seeley, J. S. et al., "Temperature-invariant and other narrow-band IR filters containing PbTe, 4-20 [micrometers]", Proceedings of the Society of Photo-Optical Instrumentation Engineers, 1980, 246, pp. 83-94.
Takahashi, H., "Temperature stability of thin-film narrow-bandpass filters produced by ion-assisted deposition", Applied Optics, 1995, 34(4), pp. 667-675.
Thelen, A., "Multilayer Filters with Wide Transmittance Bands", Journal of the Optical Society of America, 1963, 53(11), pp. 1266-1279.
Tsai, R-Y., et al., "Thermally stable narrow-bandpass filter prepared by reactive ion-assisted sputtering", Applied Optics, 2001, 40(10), pp. 1593-1598.
Weiting, F. et al., "Temperature Effects on the Refractive Index of Lead Telluride and Zinc Selenide", Infrared Physics, 1990, 30(4), pp. 371-373.
Wiechmann, S. et al., "Thermo-optic properties of TiO2, Ta2O5 and Al2O3 thin films for integrated optics on silicon", Thin Solid Films, 2009 517(24), pp. 6847-6849.
Zemel, J. N. et al., "Electrical and Optical Properties of Epitaxial Films of PbS PbSe PbTe and SnTe", Shys. Rev, 1965, 140, pp. A330-A343.
Roithner LaserTechnik GmbH Mid-IR Products Brochure, Sep. 2010, 4 pages.
Combined Search and Exam Report under Sections 17 and 18(3) in corresponding United Kingdom patent application No. 1416268.9 dated Jan. 29, 2015, 9 pages.
Exam Report under Section 18(3) in corresponding United Kingdom patent application No. 1416268.9 dated Aug. 29, 2017, 5 pages.
Search Report and Written Opinion of International Patent Application No. PCT/US2015/049094 dated Dec. 1, 2015, 13 pages.
Office Action issued in related U.S. Appl. No. 15/511,491 dated Sep. 18, 2018, 10 pages.
Combined Search and Exam Report under Sections 17 and 18(3) in corresponding United Kingdom patent application No. 1416256.4 dated Mar. 16, 2015, 6 pages.
Search Report and Written Opinion of International Patent Application No. PCT/US2015/049058 dated Dec. 23, 2015, 15 pages.
Combined Search and Exam Report under Sections 17 and 18(3) in corresponding United Kingdom patent application No. 1416257.2 dated Jan. 14, 2015, 6 pages.
Search Report and Written Opinion of International Patent Application No. PCT/US2015/049065, dated Nov. 24, 2015, 18 pages.
Combined Search and Exam Report under Sections 17 and 18(3) in corresponding United Kingdom patent application No. 1416260.6 dated Jan. 26, 2015, 5 pages.
Search Report and Written Opinion of International Patent Application No. PCT/US2015/049554, dated Dec. 23, 2015, 8 pages.
Office Action issued in related U.S. Appl. No. 15/511,343 dated Feb. 21, 2018, 26 pages.
Combined Search and Exam Report under Sections 17 and 18(3) in corresponding United Kingdom patent application No. 1416264.8 dated Mar. 16, 2015, 6 pages.
Combined Search and Exam Report under Sections 17 and 18(3) in corresponding United Kingdom patent application No. 1416265.5 dated Mar. 12, 2015, 8 pages.
Exam Report under Section 18(3) in corresponding United Kingdom patent application No. 1416265.5 dated Oct. 4, 2016, 3 pages.
Search Report and Written Opinion of International Patent Application No. PCT/US2015/049061 dated Dec. 23, 2015, 17 pages.
CSI Technologies: Analytical Testing and Analysis C54:D57//csi-tech.net/assets/literature/analytical-testing-and-analysis.pdf (CSI Industries) (2 pages).
Tropf et al: Optical materials: visible and infrared, Chapter 11 of Electro-Optics Handbook (R.W. Waynant and M.N. Ediger, eds.), Second edition, McGraw-Hill, New York (2000) 125 pages.

* cited by examiner

MID-INFRARED ACID SENSOR

Embodiments of the present disclosure relate to a mid-infrared sensor and a method of mid-infrared sensing to monitor a mineral acid dissolved in a liquid.

BACKGROUND

Online monitoring and measurement of mineral acids is problematic because of the reactivity of the acids. However, it is often important in industrial processes to have a real-time understanding of the amount of acid present in the process and/or used in the process.

The analysis of chemical composition of fluid samples from hydrocarbon wells for the determination of phase behaviour and chemical composition is a critical step in the monitoring and management of a hydrocarbon well as well as the evaluation of the producibility and economic value of the hydrocarbon reserves. Similarly, the monitoring of fluid composition during production or other operations can have an important bearing on reservoir management decisions. Similarly, determination of phase behaviour and chemical composition is important in pipelines and the like used to convey/transport hydrocarbons from the wellhead, including subsea pipelines.

Several disclosures have described analysis of specific gases in borehole fluids in the downhole environment using near-infrared (e.g. $\lambda$=1-2.5 µm) spectral measurements. For example, U.S. Pat. No. 5,859,430 describes the use of near-infrared spectroscopy to determine quantitatively the presence of methane, ethane and other simple hydrocarbons in the gas phase. The gases were detected using the absorption of near-infrared radiation by the overtone/combination vibrational modes of the molecules in the spectral region 1.64-1.75 µm.

More recently, U.S. Pat. No. 6,995,360 describes the use of mid-infrared radiation with a wavelength $\lambda$=3-5 µm to monitor gases in downhole environments, and U.S. Patent Publication No. 2012/0290208 proposes the use of mid-infrared radiation to monitor sequestered carbon dioxide dissolved into the liquid solutions of saline aquifers.

There are however many technical problems with using mid-infrared sensors in the hydrocarbon industry and processing information from such sensors. Additionally, much of the utility of mid-infrared spectroscopy with respect to acid monitoring has not previously been recognized.

SUMMARY

Embodiments of the present disclosure are at least partly based on the recognition that mineral acids can be monitored using a sensor based on mid-infrared radiation absorbance.

Accordingly, in a first aspect, embodiments of the present disclosure provide a sensor for monitoring a mineral acid dissolved in a liquid, the sensor comprising:
- an internal reflection window configured in use for contacting with the liquid;
- a mid-infrared light source configured to direct a beam of mid-infrared radiation into said window and provide for generating an attenuated internal reflection at an interface between the window and the liquid;
- a first narrow bandpass filter configured to filter internally reflected mid-infrared radiation received from the window, wherein the first narrow bandpass filter preferentially transmits mid-infrared radiation over a band of wavelengths corresponding to an absorbance peak of the dissolved mineral acid;
- an infrared detector for detecting filtered mid-infrared radiation transmitted through the first narrow bandpass filter; and
- a processor arrangement, operably coupled to the infrared detector, and configured to measure an intensity of the detected mid-infrared radiation transmitted through the first narrow bandpass filter and determine an amount (e.g. a concentration) of the mineral acid dissolved in the liquid As discussed below, the sensor may be part of a sensor arrangement e.g. with a further similar sensor for obtaining a reference intensity.

In a second aspect, embodiments of the present disclosure provide the use of the sensor, or sensor arrangement, of the first aspect to determine an amount a mineral acid dissolved in a liquid. For example, a method of monitoring a mineral acid dissolved in a liquid may include: providing the sensor of the first aspect such that the internal reflection window is in direct contact with the liquid; and operating the sensor to determine an amount of the mineral acid dissolved in the liquid.

In a third aspect, embodiments of the present disclosure provide a well tool (such as a drilling, production well or wireline sampling tool, an acidizing tool, an injection tool and/or a drilling/coiled tubing tool) including the sensor, or sensor arrangement, of the first aspect.

Optional features of the invention will now be set out. These are applicable singly or in any combination with any aspect of the invention.

The liquid may be, or may be a component of, a production fluid, drilling fluid, completion fluid or a servicing fluid.

In embodiments of the present disclosure, the term "mid-infrared radiation" means that the radiation has a wavelength in the range from about 2 to 20 µm, and in some embodiments from about 3 to 12 µm or from about 3 to 10 µm.

In embodiments of the present disclosure, the first narrow bandpass filter may be configured such that its wavelength transmission band is substantially temperature invariant over all temperatures in the range from about 25 to 150° C. Temperatures in downhole environments can vary greatly, e.g. from room temperature up to 150° C. or 200° C. By using such a temperature invariant filter, the sensitivity of the sensor to shifts in temperature of its surroundings can be greatly reduced, improving the accuracy with which the amount of the dissolved mineral acid is determined.

To cover a greater range of downhole temperatures, the wavelength transmission band of the first narrow bandpass filter may be substantially temperature invariant over all temperatures in the range from 25 to 200° C. To cover both downhole and subsea conditions (where ambient temperatures can be in the range from −25 to 25° C.), the wavelength transmission band of the first narrow bandpass filter may be substantially temperature invariant over all temperatures in the range from −25 to 150 or 200° C.

In embodiments of the present disclosure, the term "substantially temperature invariant" means that the variance is at most about 0.1 nm/° C. In some embodiments, the variance is at most about 0.05, 0.03, 0.02 or 0.01 nm/° C.

In some embodiments of the present disclosure, the filter may be an interference filter. For example, the filter may in some embodiments comprise a substrate, formed of Si, $SiO_2$, $Al_2O_3$, Ge, ZnSe and/or the like and at each opposing side of the substrate alternating high and low refractive index layers may be formed. For example, in some embodiments, the high refractive index layers may be formed of PbTe, PbSe, PbS and/or the like and the low refractive index layers may be formed of ZnS, ZnSe and/or the like.

In some embodiments of the present disclosure, the filter may comprise three or more half wavelength cavities. Many conventional filters display high band shifts with increasing temperature. For example, shifts in the range 0.2 to 0.6 nm/° C. are typical. Transmissivities of conventional filters also tend to reduce with increasing temperature. However, in embodiments of the present disclosure, by using a PbTe-based, PbSe-based, PbS-based and/or the like interference filter, it is possible to substantially reduce band shifts and transmissivity reductions. For example, a PbTe-based interference filter can, in accordance with an embodiment of the present disclosure, have a band shift of only about 0.03 nm/° C. or less. As an alternative to PbTe, PbSe or PbS, in some embodiments, the high refractive index layers may be formed of Ge or the like.

In some embodiments of the present disclosure, a reference intensity is also used in the determination of the amount of the species in the fluid. Thus a sensor arrangement may include the sensor of the first aspect and a further similar sensor which may be used to obtain this reference intensity. The further sensor can have the same features as the first sensor except that its narrow bandpass filter transmits mid-infrared radiation over a band of wavelengths corresponding to a reference portion of the absorbance spectrum of the fluid. In such a scenario, the processor arrangement can be a shared processor arrangement of both sensors.

Another option, however, is to obtain the reference intensity using the first sensor. For example, the sensor may further include a second narrow bandpass filter transmitting mid-infrared radiation over a band of wavelengths corresponding to a reference portion of the absorbance spectrum of the fluid, the or a further infrared detector detecting filtered mid-infrared radiation transmitted through the second filter, and the processor arrangement measuring the reference intensity of the detected mid-infrared radiation transmitted through the second filter and using the measured reference intensity in the determination of the amount of the species in the fluid. In some embodiments of the present disclosure, the first and second filters may be selectably positionable between a single detector and the window, or each of the first and second filters can have a respective detector. The second narrow bandpass filter may be configured such that its wavelength transmission band is substantially temperature invariant over all temperatures in the range from about 25 to 150° C. Optional features of the first narrow bandpass filter may pertain also to the second narrow bandpass filter.

In some embodiments of the present disclosure, the sensor may be able to measure the amounts of more than one mineral acid in the liquid. For example, the sensor may, in some embodiments of the present disclosure, include a plurality of the first narrow bandpass filters, each transmitting mid-infrared radiation over a band of wavelengths corresponding to an absorbance peak of a respective mineral acid, the or a respective further infrared detector detecting the filtered mid-infrared radiation transmitted through each first filter, and the processor arrangement measuring the intensity of the detected mid-infrared radiation transmitted through each first filter and determining therefrom an amount of each mineral acid dissolved in the liquid. The first filters may be selectably positionable between a single detector and the window, or each first filter can have a respective detector.

When the sensor is able to measure/monitor more than one species, the determined amounts of the species in the fluid can be in the form of a ratio of the concentrations of the species.

In some embodiments of the present disclosure, the beam of mid-infrared light/radiation may be pulsed. This may be achieved, for example, by providing a mechanical chopper between the source and the window, or by pulsing the source.

In some embodiments of the present disclosure, the source may be a broad band thermal source or a narrower band source such as a light emitting diode or a laser.

In some embodiments of the present disclosure, the detector may be a thermopile, a pyroelectric or (particularly in subsea applications, where the low ambient temperatures can provide cooling) a photodiode detector.

In some embodiments of the present disclosure, the window may be a diamond window or a sapphire window. In some embodiments of the present disclosure, the diamond window may be formed by chemical vapour deposition. Sapphire has a cut off for mid-infrared radiation at wavelengths of about 5 to 6 microns, but sapphire windows can generally be formed more cheaply than diamond windows. Thus, for absorption peaks below the cut-off (such as the $CO_2$ absorption peak at about 4.3 microns), sapphire may be an alternative to diamond. In particular, for a given cost a larger window can be formed from sapphire.

In some embodiments of the present disclosure, the sensor may further include a heater, which is operable to locally heat the window, thereby cleaning the surface of the window in contact with the fluid. Merely by way of example, in some embodiments of the present disclosure, the window may comprise a conductive or semiconductive material (e.g. an area of semiconductive boron-doped diamond or the like), and the heater may comprise an electrical power supply that sends a current through the window to induce resistive heating thereof. For example, in some embodiments of the present disclosure, the diamond window may comprise a central mid-infrared transmissive (e.g. undoped) area and an encircling area of semiconductive boron-doped diamond. The heater can induce resistive heating of the encircling area, and the central area can then be heated by conduction of heat from the encircling area. In some embodiments of the present disclosure, the heater may heat the window to a peak temperature of at least 400° C. In some embodiments of the present disclosure, the heater may maintain the peak temperature for less than one microsecond.

Alternatively or additionally, In some embodiments of the present disclosure, the sensor may further include an ultrasonic cleaner which is operable to ultrasonically clean the surface of the window in contact with the fluid. As another option, in some embodiments of the present disclosure, the sensor may be provided with a pressure pulse arrangement, which is operable to produce a pressure pulse in the fluid at the window, thereby cleaning the surface of the window in contact with the fluid. In some embodiments of the present disclosure, the arrangement may produce a pressure pulse of at least 1000 psi (6.9 MPa) in the fluid.

In some embodiments of the present disclosure, the sensor may be located downhole.

In embodiments of the present disclosure, the mineral acid may be HF, HCl, HBr or HI. In the hydrocarbon industry, HCl in particular is extensively used for stimulation of carbonate formations. The sensor in accordance with an embodiment of the present invention can allow the mineral acid concentration to be monitored to evaluate efficiency of acidisation operations, the high concentrations of mineral acids typically used in such operations often making pH measurements unsuitable. The transmission band of the first filter can be located on a dissociated H absorbance peak of about 1050 $cm^{-1}$. In embodiments of the present disclosure, the position and height of this peak tends to be insensitive to salt content in the (typically water-based) liquid.

In some embodiments of the present disclosure, a further sensor may be provided which is adapted/used for monitoring $CO_2$ concentration in the fluid. In general, attenuated total reflection mid-infrared sensing can only be used to sense condensed phases, but $CO_2$ is an exception, as it is strongly absorbing in the mid-infrared at a wavelength of about 4.3 µm. The further sensor may be similar to the mineral acid sensor (i.e. with an internal reflection window, mid-infrared light source, first narrow bandpass filters, an infrared detector, and a processor arrangement) except that instead of a first narrow bandpass filter corresponding to an absorbance peak of the dissolved mineral acid, the further filter may have three first narrow bandpass filters corresponding to respective absorbance peaks of water, oil and $CO_2$.

In addition, the processor arrangement, instead of determining an amount of the mineral acid dissolved in the liquid, can determine an amount of $CO_2$ in a fluid. Such an arrangement can allow the $CO_2$ to be monitored when the window is in contact with a fluid which can be a liquid water-based phase, a liquid oil-based phase, a mixture of liquid water and liquid oil-based phases, or a gas phase (i.e. when the window is dry). In some embodiments of the present disclosure, the sensor may also have the second narrow bandpass filter corresponding to a reference portion of the absorbance spectrum of the fluid. The transmission band of the first filters can conveniently be located at about 3330 $cm^{-1}$ (water), 2900 $cm^{-1}$ (oil) and 2340 $cm^{-1}$ ($CO_2$). The transmission band of the second filter can conveniently be located at about 2500 $cm^{-1}$.

In some embodiments of the present disclosure, both the mineral acid sensor and the $CO_2$ sensor are used in the same sensor system. In such a sensor system, the mineral acid sensor can provide a measure of how much acid is being deployed to stimulate a carbonate formation, and the $CO_2$ sensor, by measuring the amount of $CO_2$ produced (by dissolution of carbonate), can provide a measure of the effectiveness of that acid deployment. Indeed the two sensors may be combined in one tool.

Accordingly, another aspect of the invention provides a method of stimulating production from a well including:
  injecting a liquid containing dissolved mineral acid into the well to stimulate production from a carbonate formation;
  providing the sensor of the first aspect such that the internal reflection window is in direct contact with the liquid;
  operating the sensor to determine the amount of mineral acid deployed into the formation;
  providing a further sensor for monitoring $CO_2$ in a fluid, the further sensor including: a further internal reflection window which, in use, is in direct contact with a fluid; a further mid-infrared light source which directs a beam of mid-infrared radiation into said further window for attenuated internal reflection at an interface between the further window and the fluid; three further first narrow bandpass filters which preferentially transmit mid-infrared radiation over bands of wavelengths corresponding to respective absorbance peaks of water, oil and $CO_2$ to filter internally reflected mid-infrared radiation received from the window; one or more further infrared detectors which detect filtered mid-infrared radiation transmitted through the further first filters; and a further processor arrangement, operably coupled to the infrared detector(s), which measures the intensity of the detected mid-infrared radiation transmitted through the first filters, and determines therefrom an amount of $CO_2$ in the fluid notwithstanding whether the fluid contacting the further window is a liquid water-based phase, a liquid oil-based phase, a mixture of liquid water and liquid oil-based phases, or a gas phase; and
  operating the further sensor to determine an amount of $CO_2$ in the fluid produced by the formation.

BRIEF DESCRIPTION OF THE DRAWINGS

Embodiments of the invention will now be described by way of example with reference to the accompanying drawings in which.

Figure 1A:
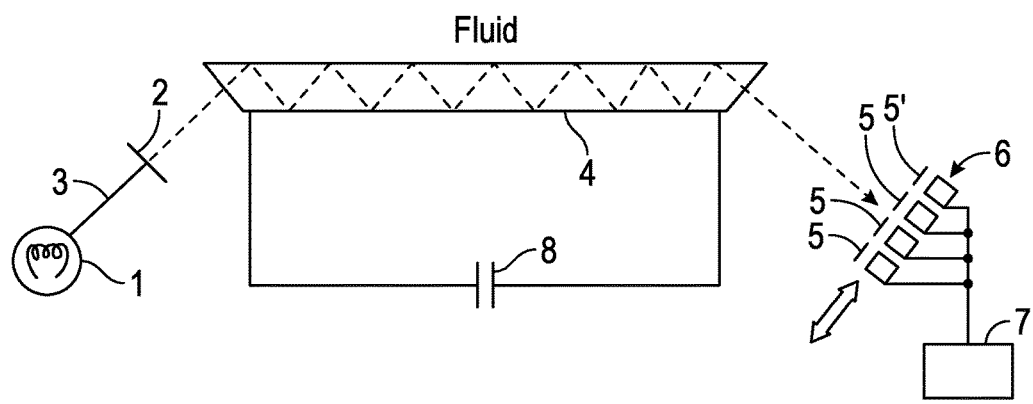
FIG. 1 shows schematically (a) a mid-infrared sensor, in accordance with an embodiment of the present disclosure, and (b) the sensor implemented as a module in a toolstring.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention, it being understood that various changes may be made in the function and arrangement of elements without departing from the scope of the invention.

Specific details are given in the following description to provide a thorough understanding of the embodiments. However, it will be understood by one of ordinary skill in the art that embodiments maybe practiced without these specific details. For example, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1(a) shows schematically a mid-infrared sensor, in accordance with an embodiment of the present disclosure, comprising a thermal broad band mid-infrared source 1, a mechanical chopper 2 that pulses a beam 3 of mid-infrared radiation which issues from the source, a diamond window 4, a set of selectively movable first narrow bandpass filters 5 and a second narrow bandpass filter 5', respective mid-infrared detectors 6 for the filters, and a processor arrangement 7. The sensor may be encased in a protective housing which allows the sensor to be deployed downhole, the window 4 being positioned for contact with the fluid to be monitored. In some embodiments of the present disclosure, mid-infrared waveguides (not shown) may optically connect the source, window and the detectors. Suitable waveguides can be formed from optical fibres (e.g. hollow fibres or chalcogenide fibres), solid light pipes (e.g. sapphire pipes), or hollow light pipes (e.g. air or vacuum filled) with a reflective (e.g. gold) coating.

As the output from detector 6 changes with temperature, even small changes in temperature may cause a large drift in signal output. However, in some embodiments of the present disclosure, pulsing the beam 3 allows the output signal of the detector to be frequency modulated, enabling removal of the environmental temperature effects from the signal. More particularly, the environment effects can be largely removed electronically by a high pass filter, because the time constant for environment effects tends to be much longer than the signal frequency. In some embodiments of the present disclosure, the detector output is AC-coupled to an amplifier. The desired signal can then be extracted e.g. electronically by lock-in amplification or computationally by Fourier transformation.

Instead of the thermal source 1 and the mechanical chopper 2, in some embodiments of the present disclosure, the pulsed beam 3 may be produced by a pulsable thermal source, light emitting diode or laser source and/or the like. Pulsing the source in this way can give the same benefit of frequency modulation measurement, plus it may reduce resistive heating effects.

The beam 3 enters at one edge of the window 4, and undergoes a number of total internal reflections before emerging from the opposite edge. The total internal reflection of the infrared radiation at the fluid side of the window is accompanied by the propagation of an evanescent wave into the fluid. As the fluid preferentially absorbs certain wavelengths, depending on its chemical composition, this causes the emerging beam to have a characteristic variation in intensity with wavelength.

In some embodiments of the present disclosure, the window 4 may be mechanically able to withstand the high pressures and temperatures typically encountered downhole. In some embodiments of the present disclosure, the window may be chemically stable to fluids encountered downhole and transparent in the mid-IR wavelength region. In some embodiments of the present disclosure, the window may comprise diamond, sapphire and/or the like.

The first narrow bandpass filters 5 each transmit mid-infrared radiation over a band of wavelengths corresponding to an absorbance peak of a respective species in the fluid, while the second narrow bandpass filter 5' transmits mid-infrared radiation over a band of wavelengths corresponding to a reference portion of the absorbance spectrum of the fluid. The beam 3 then passes through a selected one of the narrow bandpass filters and is detected at the respective detector 6. Instead of having a plurality of detectors, each movable with its corresponding filter (as indicated by the double-headed arrow), a further option is to have a single detector in front of which the filters are selectively movable.

The detector 6 can be e.g. semiconductor photo-diodes (particularly in subsea applications), thermopiles or pyroelectric detectors.

In an embodiment of the present disclosure the processor arrangement 7 receives a signal from the respective detector 6, which it processes to measure the intensity of the detected mid-infrared radiation transmitted through each filter 5, 5', and may either detect the respective species in the fluid or determine from the measured intensity, as discussed in more detail below, an amount of the respective species in the fluid.

Also discussed in more detail below, the sensor comprise have a heater 8 which is operable to locally heat the window 4, thereby cleaning the surface of the window in contact with the fluid. Other options, however, are to clean the window ultrasonically (as described for example in U.S. Pat. No. 7,804,598 incorporated by reference herein for all purposes), or with a mechanical wiper.

Figure 1B:
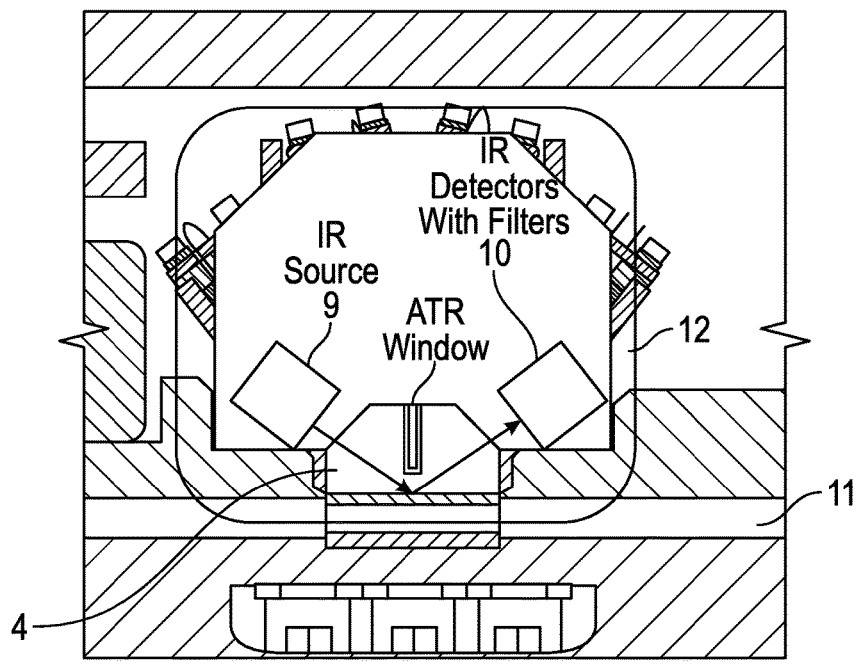

FIG. 1(*b*) shows schematically how the sensor, in accordance with embodiments of the present disclosure may be implemented as a module in a toolstring. In an embodiment of the present disclosure, the source 1 and chopper 2 may be contained in a source unit 9 and filters 5, 5' and detectors 6 may be contained in a detector unit 10. These are located close to the window 4 that is in contact with a tool flowline 11. In some embodiments of the present disclosure, the sensor is packaged in a protective metal chassis 12 to withstand the high pressure of the fluid in the flowline. In some embodiments of the present disclosure, the window is sealed into the chassis also to withstand the high pressures, and its packaging ensures no direct source light strays into the detectors.

Narrow Bandpass Filters

Figure 2:
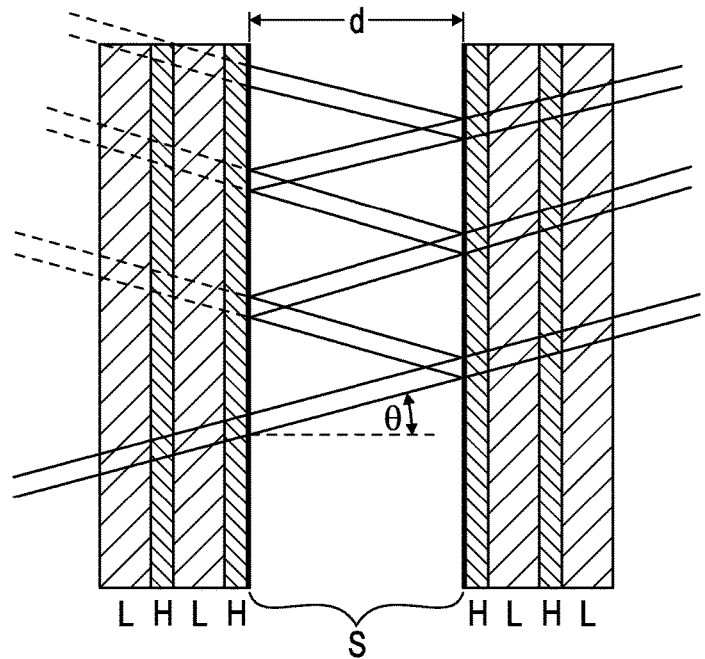
FIG. 2 shows schematically a narrow bandpass filter based on Fabry-Perot interferometry, in accordance with an embodiment of the present disclosure.

In some embodiments of the present disclosure, the narrow bandpass filters 5, 5' may be based on Fabry-Perot interferometry. As shown in FIG. 2, in some embodiments of the present disclosure, each filter may comprise a substrate S of low refractive index and thickness d. On opposing surfaces of the substrate are stacked alternating high-reflectivity dielectric layers of high H and low L refractive index deposited onto the substrate using techniques such as ion-beam sputtering or radical-assisted sputtering. Each layer in the stacks of alternating layers of high H and low L refractive index has an optical thickness of a quarter wavelength.

In an embodiment of the present disclosure, the optical thickness nd cos θ of the substrate S, where n is the refractive index of the substrate, is equal to an integer number of half wavelengths $\lambda_m$, where $\lambda_m$ is the peak transmission wavelength, corresponding approximately to the centre wavelength of the pass band of the filter. The condition for the transmission of radiation of wavelength $\lambda_m$ through the filter is thus $m\lambda_m/2 = nd \cos\theta$, where m is an integer.

The spectral region of conventional narrow bandpass dielectric filters designed to operate in the mid-infrared spectral regions shifts systematically to longer wavelengths with increasing temperature. The origin of the change in $\lambda_m$ with temperature is a change in the material properties with temperature of the dielectric materials that comprise the layers of the filter.

However, in accordance with embodiments of the present disclosure, an approach for the configuration and fabrication of mid-infrared narrow bandpass filters is provided where the filters have substantially temperature invariant optical properties over a wide temperature range.

In accordance with embodiments of the present disclosure, the approach can be considered by the design of the filter:

$$(LH)^{x1}(LL)^{y1}(HL)^{x2}(LL)^{y2}\ldots(LL)^{yN}(HL)^{xN+1}$$

consisting of a total of y half wavelength spacers (cavities) LL of low refractive index material in N cycles ($y=\Sigma y_i$), LH being the stacks of $x_i$ quarter wavelength layers of alternating of high and low refractive index material in the N cycles. The reflections wavelength of the quarter wavelength reflector stack (which is the only reflection to undergo constructive interference), irrespective of the values of $x_i$ and N, can be expressed as:

$$\lambda_m = 2(n_L d_L + n_H d_H)$$

for first order reflections (m=0). The temperature variation of the wavelength in the reflector stack $d\lambda_m/dT|_s$ can be expressed as:

$$\frac{d\lambda_m}{dT}\bigg|_s = 2n_L d_L\left(C_L + \frac{dn_L}{n_L dT}\right) + 2n_H d_H\left(C_H + \frac{dn_H}{n_H dT}\right)$$

where $C_L$ and $C_H$ are the coefficients of linear expansion of the low and high refractive index materials, respectively. From eqn. [1] for first order reflection and normal incidence (i.e., m=1 and θ=0°), the corresponding temperature dependence $d\lambda_m/dT|_c$ of the cavity layer of low refractive index material is given by:

$$\frac{d\lambda_m}{dT}\bigg|_c = 2yn_L d_L\left(C_L + \frac{dn_L}{n_L dT}\right)$$

noting that y is the total number of half wavelength cavity layers. The total change in wavelength with temperature $d\lambda_m/dT|_T$ is given by the sum of $d\lambda_m/dT|_c$ and $d\lambda_m/dT|_s$:

$$\frac{d\lambda_m}{dT}\bigg|_T = 2(1+y)n_L d_L\left(C_L + \frac{dn_L}{n_L dT}\right) + 2n_H d_H\left(C_H + \frac{dn_H}{n_H dT}\right)$$

-continued or $$\left.\frac{d\lambda_m}{\lambda_m dT}\right|_T = (1+y)\left(C_L + \frac{dn_L}{n_L dT}\right) + \left(C_H + \frac{dn_H}{n_H dT}\right)$$

noting that $n_L d_L = n_H d_H$ at the temperature for which the filter is designed for use. Clearly $d\lambda_m/dT|_T$ can only be zero if the value of $dn/dT$ for one of the materials is negative. This condition can be fulfilled by high refractive index materials such as PbTe, PbSe or PbS. For close matching of the value of $d\lambda_m/dT|_T$ to zero, the wavelength dependence of n, temperature and wavelength dependence of $dn_i/dT$ can be taken into account.

The condition $d\lambda_m/dT|_T = 0$ is given approximately by:

$$\frac{dn_H}{n_H dT} = -(1+y)\frac{dn_L}{n_L dT}$$

noting that $C_i$ is considerably smaller than $dn_i/n_i dT$ for most materials used in mid-infrared filters. The term (1+y) can be chosen to satisfy the above expression depending on the choice of low refractive index material. For example, with ZnSe and PbTe for the low and high refractive index materials, respectively, and using the material values of bulk phases $n_L = 2\ 0.43$, $n_H = 6.10$, $dn_L/dT = 6.3 \times 10^{-5}\ K^{-1}$ and $dn_H/dT = -2.1 \times 10^{-3}\ K^{-1}$ for $\lambda_m = 3.4\ \square\ m$, the expression is satisfied with $y=13.3$, i.e., approximately 13 half wavelength cavity layers are required to achieve the condition $d\lambda_m/dT|_T = 0$.

There is considerable variation in the values of the material properties ($n_H$, $dn_H/dT$, $C_H$, etc.) that appear in for thin films in a multilayer structure and therefore in the predicted value of $d\lambda_m/\lambda_m dT$ or the value of y required to achieve the condition $d\lambda_m/\lambda_m dT = 0$. The uncertainty is particularly severe for the value of $dn_H/dT$ for PbTe in view of its magnitude and influence on the value of y. For example, the value of $dn/dT$ for PbTe at $\lambda_m = 5\ \square m$ has been reported to be $-1.5 \times 10^{-3}\ K^{-1}$ by Zemel, J. N., Jensen, J. D. and Schoolar, R. B., "ELECTRICAL AND OPTICAL PROPERTIES OF EPITAXIAL FILMS OF PbS, PbSe, PbTe AND SnTe", *Phys. Rev.* 140, A330-A343 (1965), $-2.7 \times 10^{-3}\ K^{-1}$ by Piccioli, N., Besson, J. M. and Balkanski, M., "OPTICAL CONSTANTS AND BAND GAP OF PbTe FROM THIN FILM STUDIES BETWEEN 25 AND 300° K", *J. Phys. Chem. Solids*, 35, 971-977 (1974), and $-2.8 \times 10^{-3}\ K^{-1}$ by Weiting, F. and Yixun, Y., "TEMPERATURE EFFECTS ON THE REFRACTIVE INDEX OF LEAD TELLURIDE AND ZINC SELENIDE", *Infrared Phys.*, 30, 371-373 (1990). From the above expression, the corresponding values of y (to the nearest integer) are 9, 17 and 18, respectively.

In view of the uncertainties in the value of $dn/dT$ for PbTe and therefore the number of low refractive index half wavelength spacers required to achieve $d\lambda_m/dT = 0$, a more useful approach is to determine the experimental value of $d\lambda_m/dT$ as a function of the optical thickness of the low refractive index cavities for a suite of filters fabricated by the same method.

Figure 3:
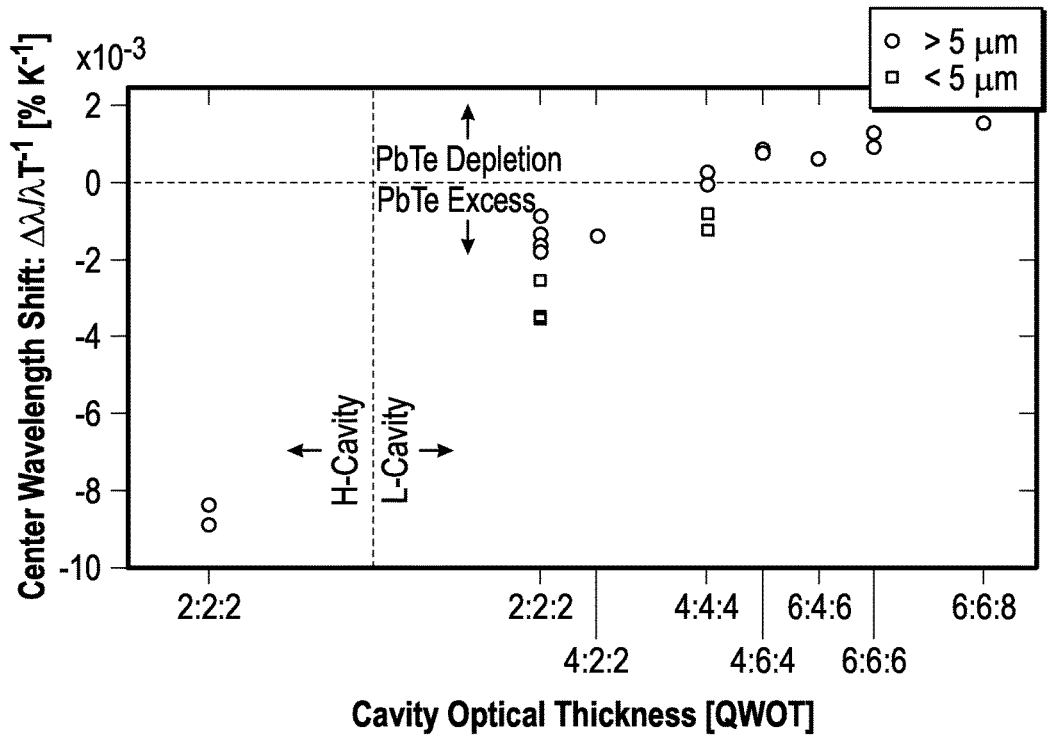
FIG. 3 shows variation of $d\lambda_m/\lambda_m dT$ for a suite of filters fabricated with ZnSe as the low refractive index material and PbTe as the high refractive index material, in accordance with an embodiment of the present disclosure.

FIG. 3 shows the variation of $d\lambda_m/\lambda_m dT$ for a suite of filters fabricated with ZnSe as the low refractive index material and PbTe as the high refractive index material. The plot shows that a particular value of $d\lambda_m/\lambda_m dT$ can be achieved by controlling the ratio of low to high refractive index materials in the filter (i.e., a parameter similar to y in the above expression). FIG. 3 shows that for $\lambda_m < 5\ \mu m$, the condition $d\lambda_m/\lambda_m dT = 0$ is met by a 4:4:4 (i.e., 3 full wavelength or 6 half wavelength cavities (y=6)) filter, while for $\lambda_m > 5\ \square m$ a 6:4:6 (y=8) filter is required.

The approach illustrated by FIG. 3 can be used, in accordance with an embodiment of the present disclosure, to fabricate substantially temperature invariant filters over the entire mid-infrared spectral range. In some embodiments of the present disclosure, the substrate may be formed of Si, $SiO_2$, $Al_2O_3$, Ge or ZnSe. In some embodiments of the present disclosure, high refractive index layers can be formed of PbTe, PbSe or PbS, although Ge is also an option. In some embodiments of the present disclosure, the low refractive index layers can be formed of ZnS or ZnSe.

Figure 4A:
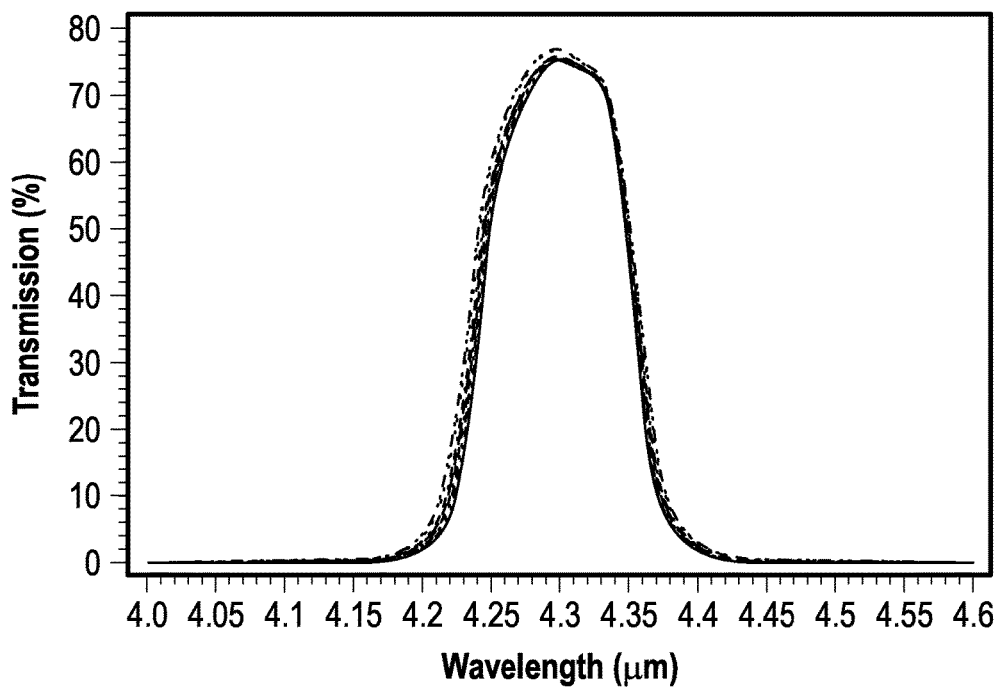
FIG. 4 shows plots of transmissivity against wavelength at a range of temperatures from 25 to 200° C. for (a) a PbTe-based filter having a pass band centred at 4.26 µm, and (b) a PbTe-based filter having a pass band centred at 12.1 µm, in accordance with embodiments of the present disclosure.
Figure 4B:
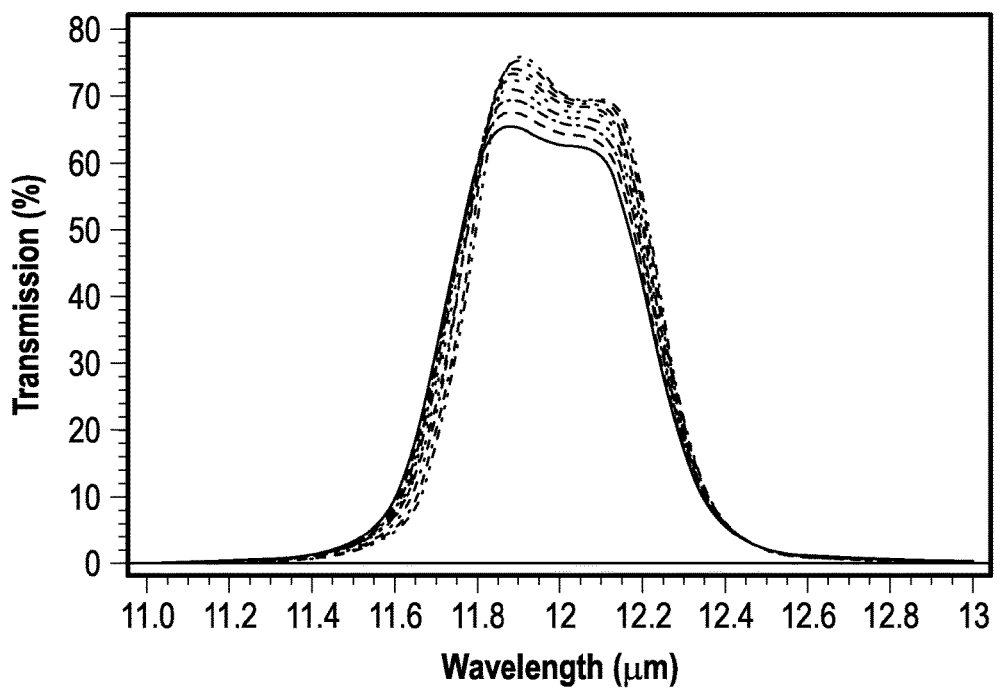

FIG. 4 shows plots of transmissivity against wavelength at a range of temperatures from 25 to 200° C. for (a) a PbTe-based filter having a pass band centred at 4.26 μm with optimum optical matching to the substrate and 3 full wavelength thickness cavities (4:4:4), and (b) a degenerate PbTe-based filter having a pass band centred at 12.1 μm with 3 half wavelength cavities (2:2:2). Similar filters can be produced having pass bands centred at other mid-infrared wavelengths. The value of $d\lambda_m/dT$ for the $\lambda_m = 4.26\ \square m$ (4:4:4) filter varies from −0.04 nm/K at 20° C. to +0.03 nm/K at 200° C. and is essentially zero over the temperature range 80-160° C. The value of $d\lambda_m/dT$ for the $\lambda_m = 12.1\ \square m$ (2:2:2) filter is −0.21 nm/K, over the temperature range 20-200° C. This allows such filters to deployed downhole, where temperatures can vary from about 25 to 200° C., without the pass band of the filter shifting to such an extent that it no longer corresponds to the absorbance peak of its respective species.

Spectroscopy

Figure 5A:
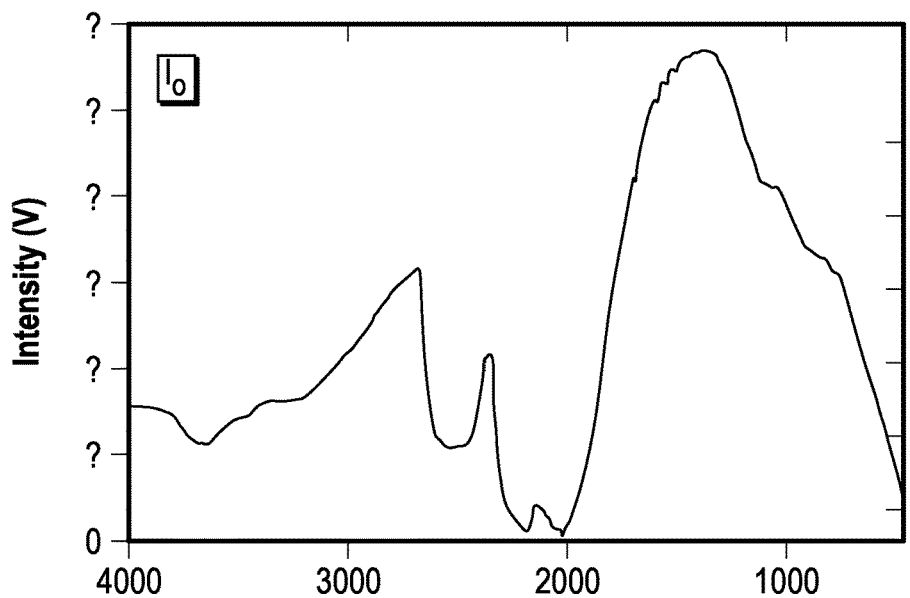
FIG. 5 shows (a) a reference intensity spectrum $I_O$ obtained from a fluid not containing a given species, (b) an intensity spectrum I obtained from the fluid containing the species, and (c) the absorbance spectrum of the species.
Figure 5B:
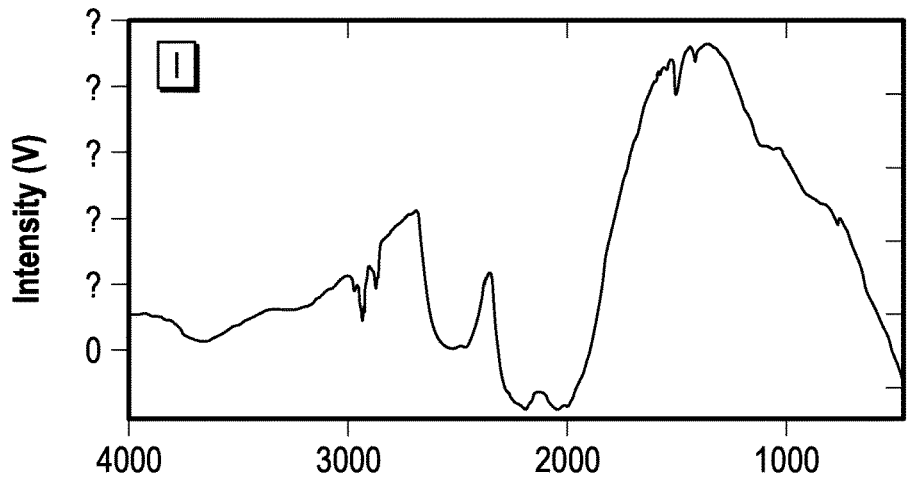
Figure 5C:
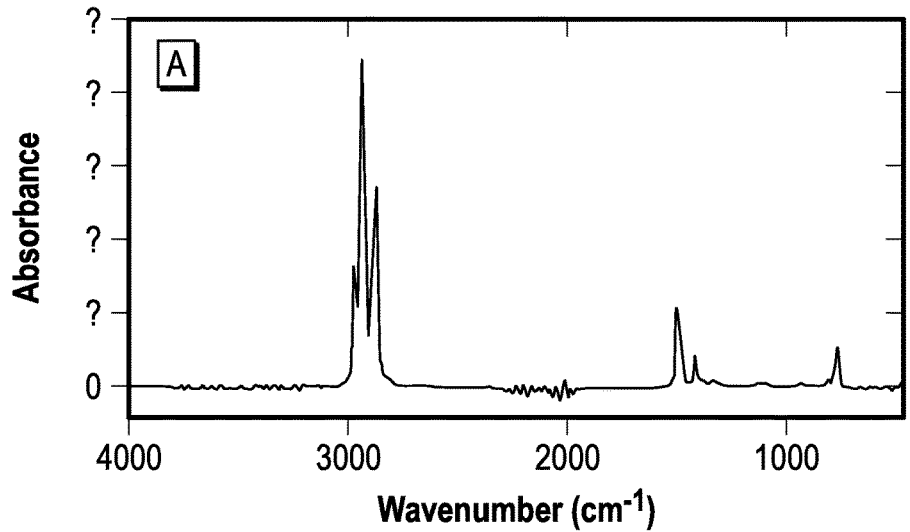

The Beer-Lambert law applied to the sensor of FIG. 1 provides that:

$$A = -\log_{10}(I/I_0)$$

where A is the absorbance spectrum by a species in the fluid having an absorbance peak at a wavelengths corresponding to the pass band of the filter 5, I is the intensity spectrum of the infrared radiation detected by the detector 6, and $I_0$ is a reference intensity spectrum. For example, FIG. 5 shows (a) a reference intensity spectrum $I_0$ obtained from a fluid not containing a given species, (b) an intensity spectrum I obtained from the fluid containing the species, and (c) the absorbance spectrum of the species.

Figure 6:
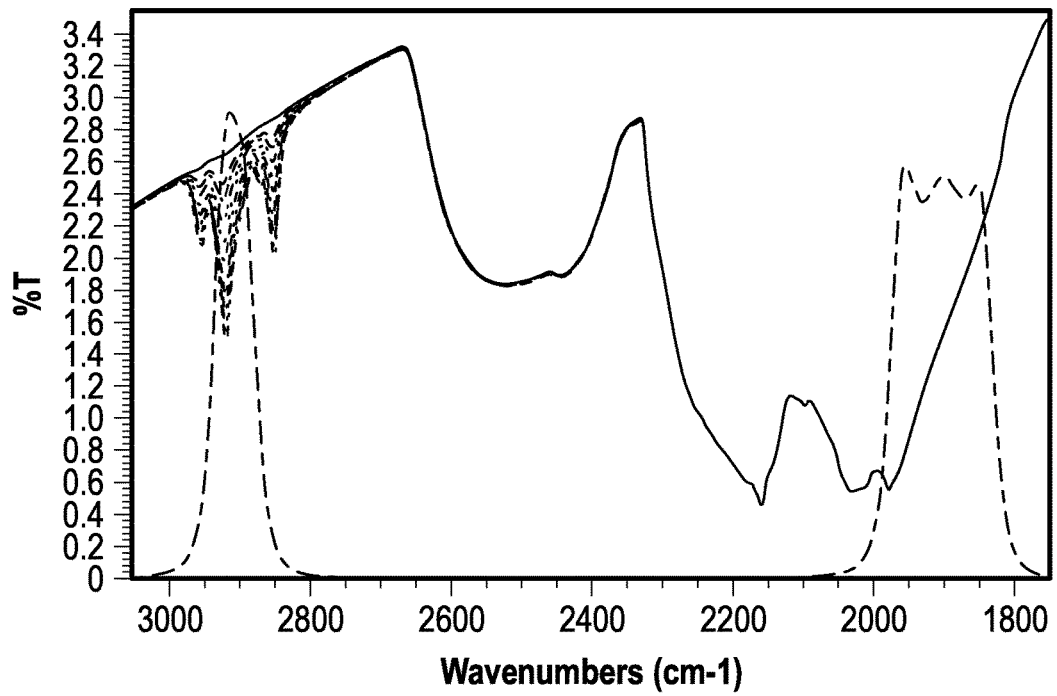
FIG. 6 shows intensity spectra obtained for dodecane dissolved in deuterated chloroform for increasing concentrations of dodecane, the spectra being superimposed with transmissivity plots for a first filter having a pass band of 3000 to 2800 $cm^{-1}$, and a second filter having a pass band of 2000 to 1800 $cm^{-1}$.

FIG. 6 shows intensity spectra obtained for dodecane dissolved in deuterated chloroform for increasing concentrations of dodecane. With increasing hydrocarbon content there is increased absorption in a first wavenumber range of 3000 to 2800 cm$^{-1}$. Conversely, the increasing hydrocarbon content has substantially no effect on absorption in a second wavenumber range of 2000 to 1800 cm$^{-1}$. The second range can thus be used as the reference to the first range. Superimposed on FIG. 6 are transmissivity plots for a first filter having a pass band of 3000 to 2800 cm$^{-1}$, and a second filter having a pass band of 2000 to 1800 cm$^1$. Two spectra are thus, in effect, detected by the filters, the first spectrum being the unfiltered spectrum multiplied by the transmissivity of the first filter and the second sub-spectrum being the unfiltered spectrum multiplied by the transmissivity of the second filter. The pass band areas of the spectra (as determined by the strengths of the signals received by the photodiode detectors), correspond to respective intensity measurements BA and $BA_0$. These are thus used to calculate a modified absorbance A' for dodecane dissolved in deuterated chloroform which is $\ln(BA/BA_0)$.

Figure 7:
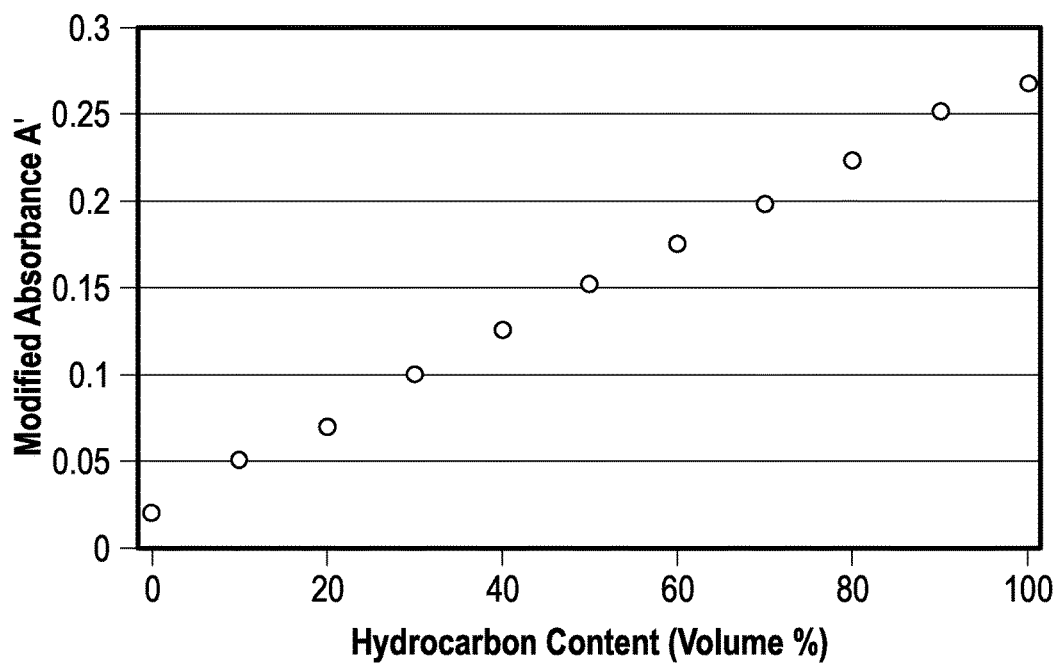
FIG. 7 shows a plot of modified absorbance A' against hydrocarbon content for dodecane dissolved in deuterated chloroform.

FIG. 7 shows a plot of modified absorbance A' against hydrocarbon content for dodecane dissolved in deuterated chloroform. The plot exhibits an approximately linear relationship between A' and hydrocarbon content.

Figure 8:
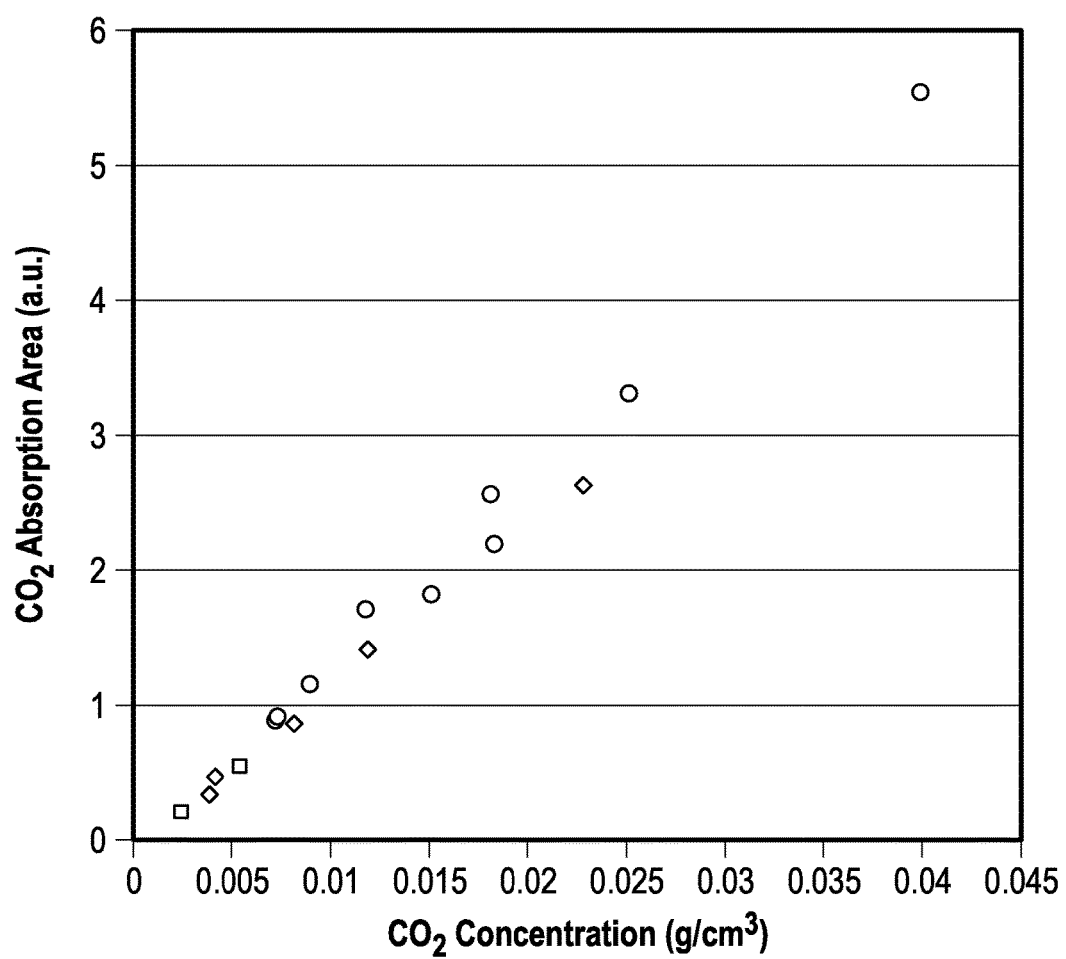
FIG. 8 shows a plot of absorbance against dissolved $CO_2$ concentration in water or hydrocarbon.

Other species can be monitored in this way. For example, FIG. 8 shows a plot of absorbance against dissolved $CO_2$ concentration in water or hydrocarbon under the high partial pressures and temperatures typical of oil field wellbore conditions.

Mineral Acid Concentration

A mid-infrared sensor, of the type discussed above, may be used to monitor mineral acid concentrations. For example, HCl is extensively pumped in coiled tubing for stimulation of carbonate formations. The high mineral acid concentration typically used in such operations often makes pH measurements unsuitable. However, the sensor can be deployed to enable HCl concentration to be monitored to evaluate acidisation efficiency. The ability of the sensor to operate under a full range of downhole temperatures is advantageous.

Figure 9:
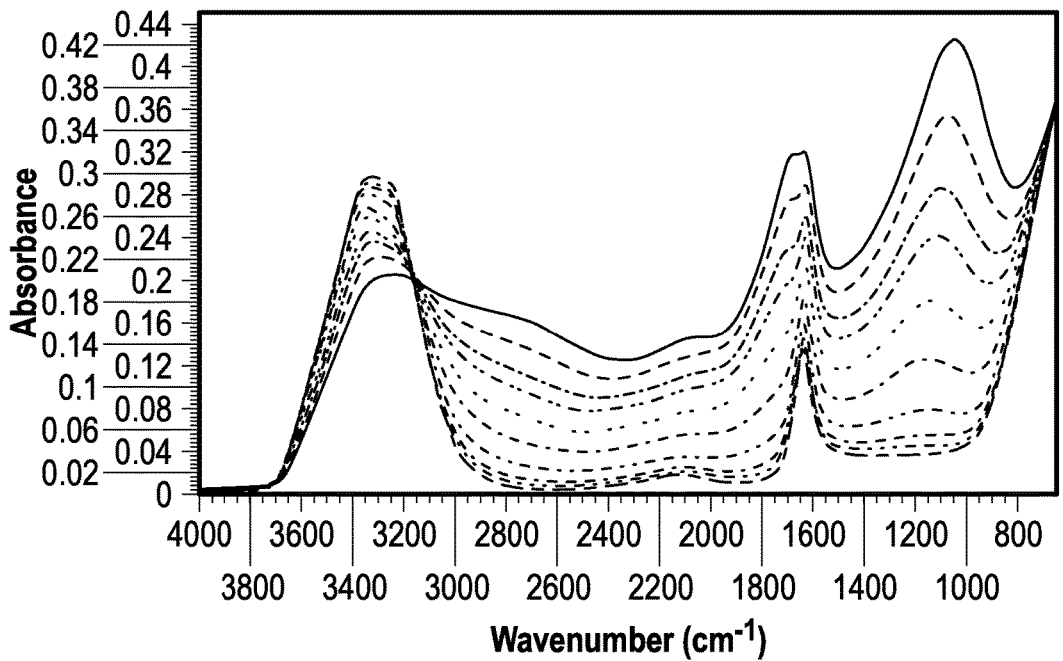
FIG. 9 shows mid-infrared absorbance spectra of HCl in water, for different HCl concentrations from 0 to 40 wt %.
Figure 10:
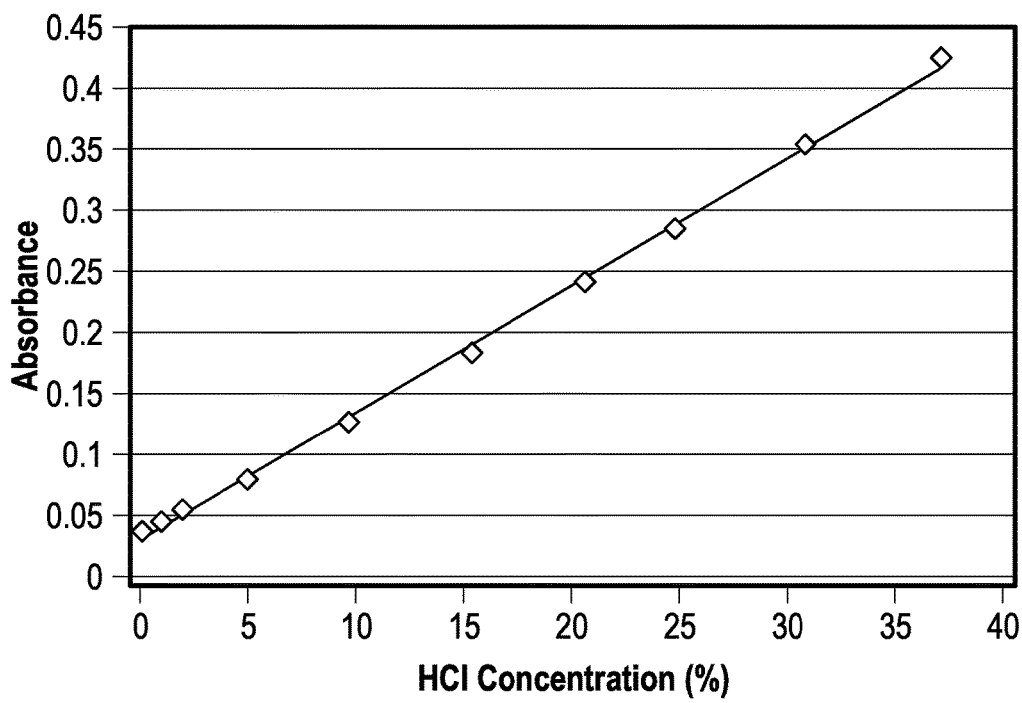
FIG. 10 shows a plot of absorbance against HCl concentration for HCl in water.

FIG. 9 shows mid-infrared absorbance spectra of HCl in water, for different HCl concentrations from 0 to 40 wt %, and FIG. 10 shows a plot of absorbance against HCl concentration for HCl in water, using a band located on the 1050 $cm^{-1}$ absorbance peak and a band corresponding to a reference portion of the absorbance spectrum. The plot of FIG. 10 demonstrates good linearity between absorbance and concentration. NaCl is not a factor with respect to HCl use in the petrochemical industry, however, $CaCl$ will be a return product in downhole HCl applications.

Figure 11:
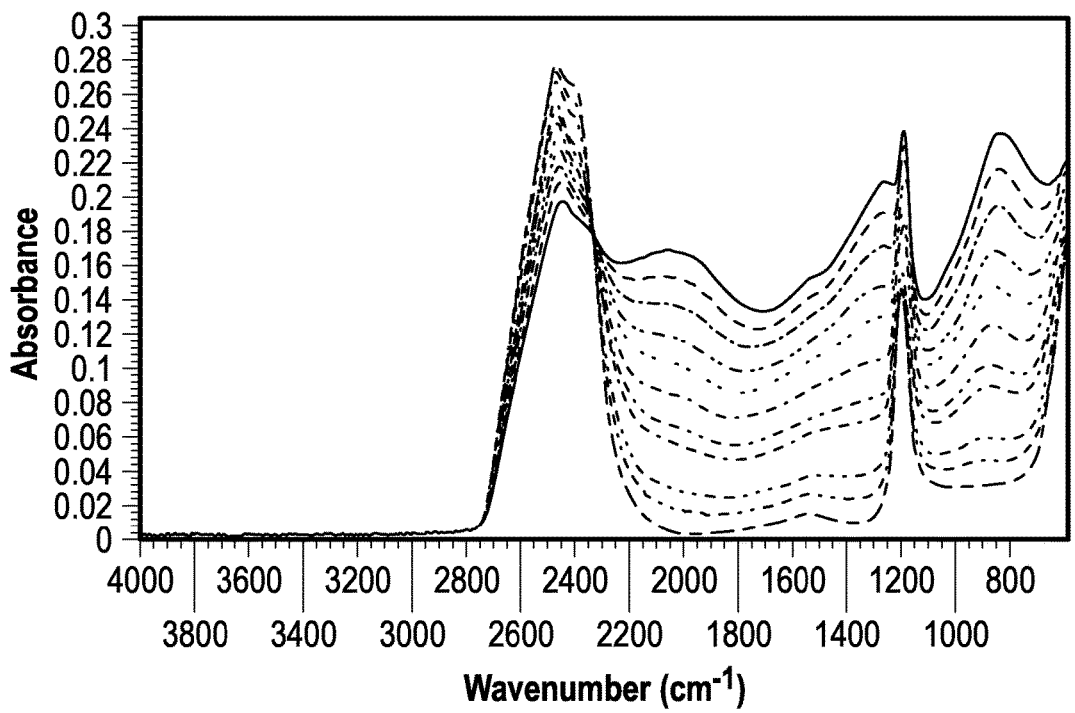
FIG. 11 shows mid-infrared absorbance spectra of DCl in $D_2O$, for different DCl concentrations from 0 to 35 wt %.
Figure 12:
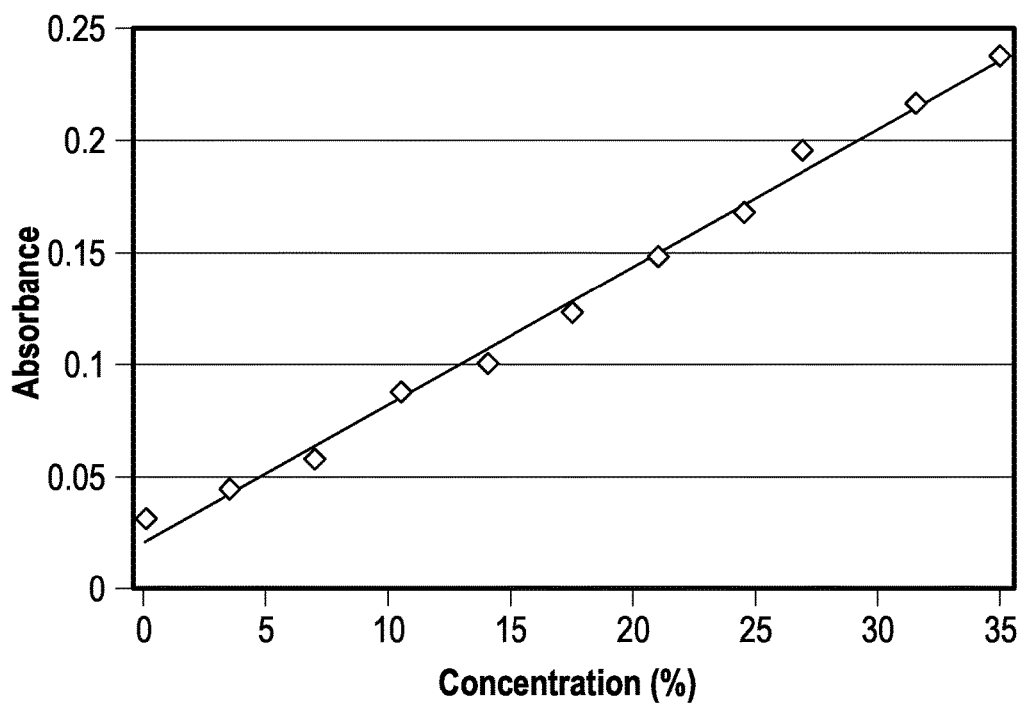
FIG. 12 shows a plot of absorbance against DCl concentration for DCl in $D_2O$.

The 1050 $cm^{-1}$ absorbance peak is apparently due to dissociated HCl, the peak only emerging as the HCl concentration rises. Further evidence that the peak is due to dissociated HCl comes from measurements of DCl in $D_2O$. FIG. 11 shows mid-infrared absorbance spectra of DCl in $D_2O$, for different DCl concentrations from 0 to 35 wt %. As expected, all the peaks shown in FIG. 9 are shifted in FIG. 11 to lower wavenumbers by approximately $1/\sqrt{2}$. For completeness, FIG. 12 shows a plot of absorbance against DCl concentration for DCl in $D_2O$, using a band located on the 850 $cm^{-1}$ absorbance peak (shifted from 1050 $cm^{-1}$ in FIG. 9) and a band corresponding to a reference portion of the absorbance spectrum.

Figure 13:
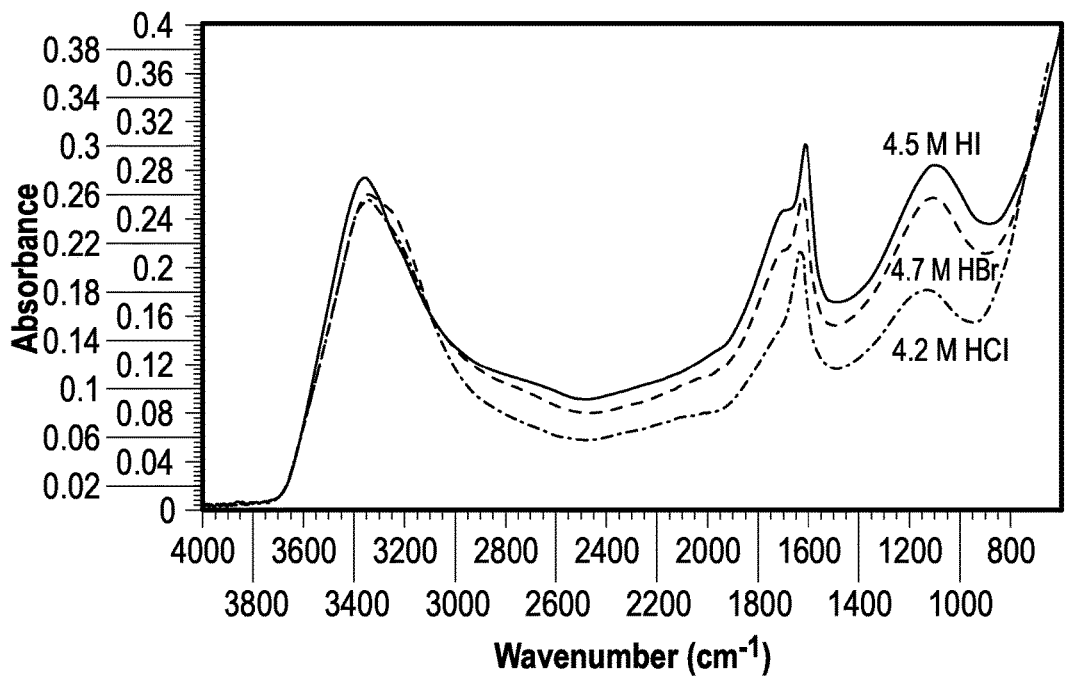
FIG. 13 shows mid-infrared absorbance spectra of 4.2 M HCl in water, 4.7 M HBr in water and 4.5 M HI in water.
Figure 14:
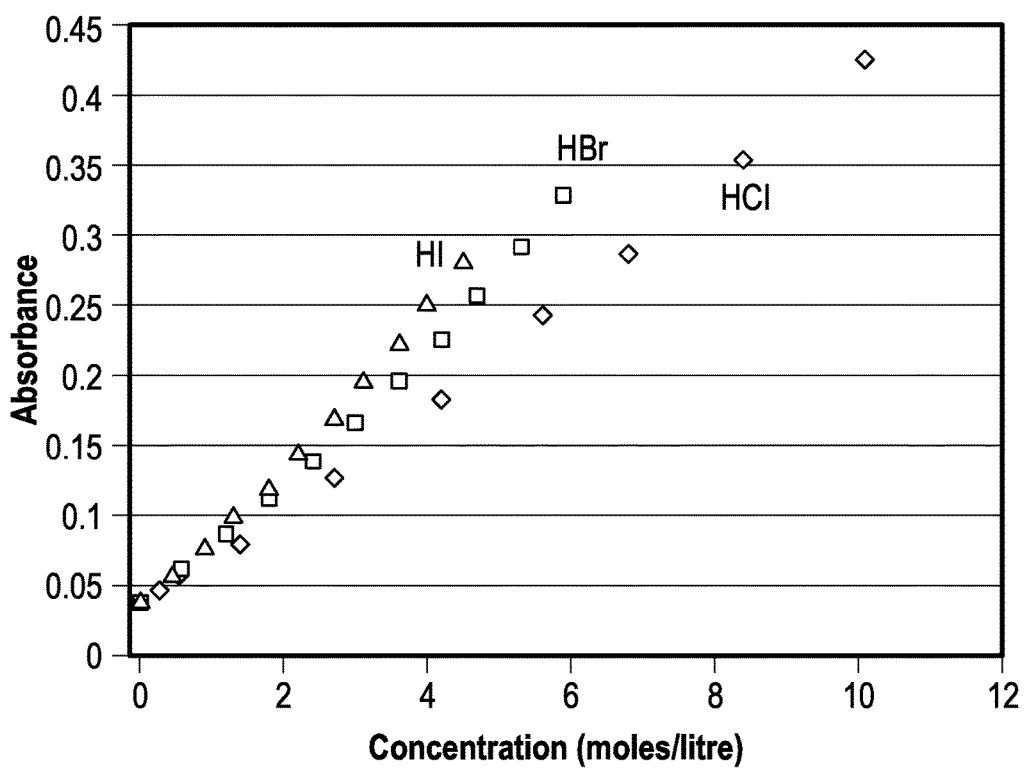
FIG. 14 shows the plots of absorbance against acid concentration for HCl, HBr and HI in water.

The 1050 $cm^{-1}$ absorbance peak is also exhibited by HBr and HI, as illustrated by FIG. 13 which shows mid-infrared absorbance spectra of 4.2 M HCl in water, 4.7 M HBr in water and 4.5 M HI in water, suggesting that the peak is caused by a hydrated proton. FIG. 14 shows the corresponding plots of absorbance against acid concentration using a band located on the 1050 $cm^{-1}$ absorbance peak.

Carbon Dioxide Concentration

Another possible use for the sensor of the type discussed above is to monitor $CO_2$ concentrations. The analysis of fluid samples from hydrocarbon wells for the determination of phase behaviour and chemical composition is a critical step in the evaluation of the producibility and economic value of the hydrocarbon reserves. An important factor in determining the economic value of gas and liquid hydrocarbon reserves is their chemical composition, particularly the concentration of gaseous components, such as carbon dioxide. Similarly, the monitoring of fluid composition during production operations can have an important bearing on reservoir management decisions, such as ceasing production from certain zones or applying chemical treatments to producing wells.

A mid-infrared sensor, of the type discussed above, may be used to monitor $CO_2$ concentrations downhole. In particular, the sensor may have three narrow bandpass filters 5 corresponding to respective absorbance peaks of water, oil and $CO_2$, and a second narrow bandpass filter 5' for a reference portion of the absorbance spectrum. Such an arrangement allows the $CO_2$ concentration to be determined when the window 4 is wetted by a liquid water phase, a liquid oil phase, a mixture of liquid water and liquid oil phases, or when the window is dry.

Figure 15A:
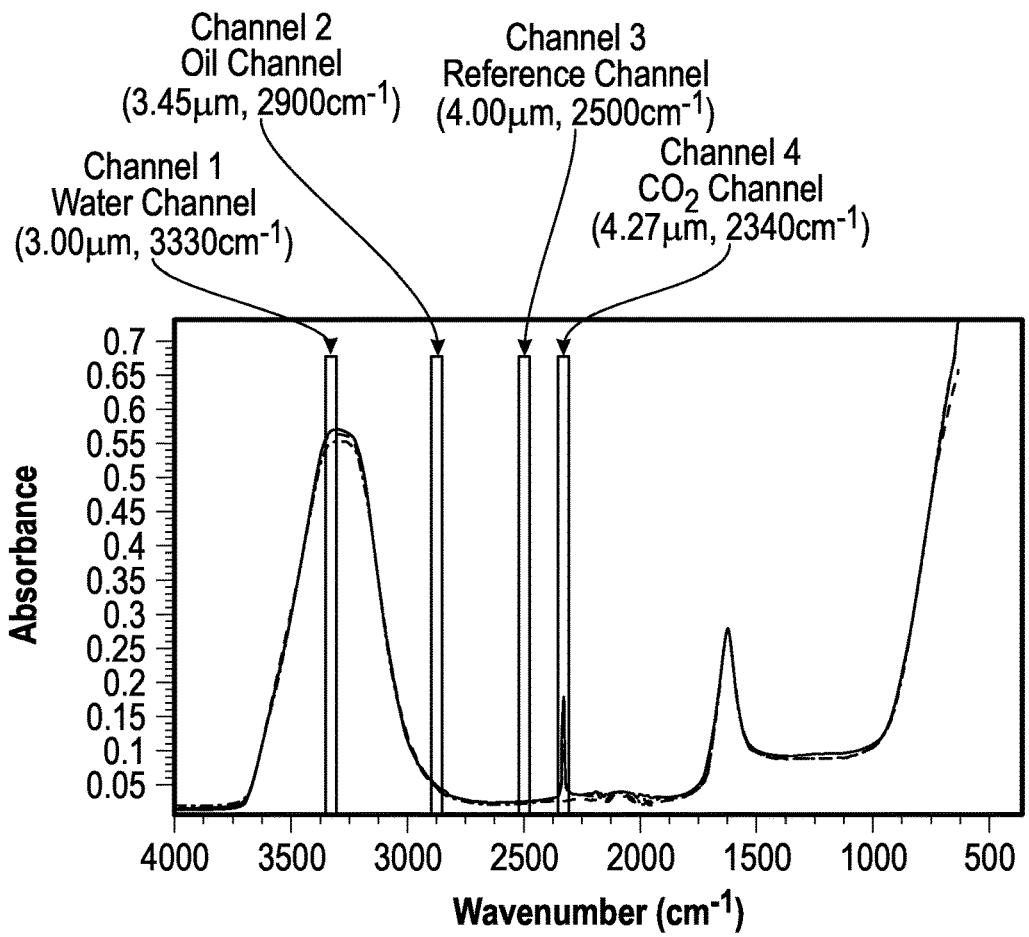
FIG. 15 shows (a) a mid-infrared absorbance spectrum for a water phase and $CO_2$, and (b) a corresponding plot of absorbance against $CO_2$ concentration for $CO_2$ in $H_2O$.
Figure 15B:
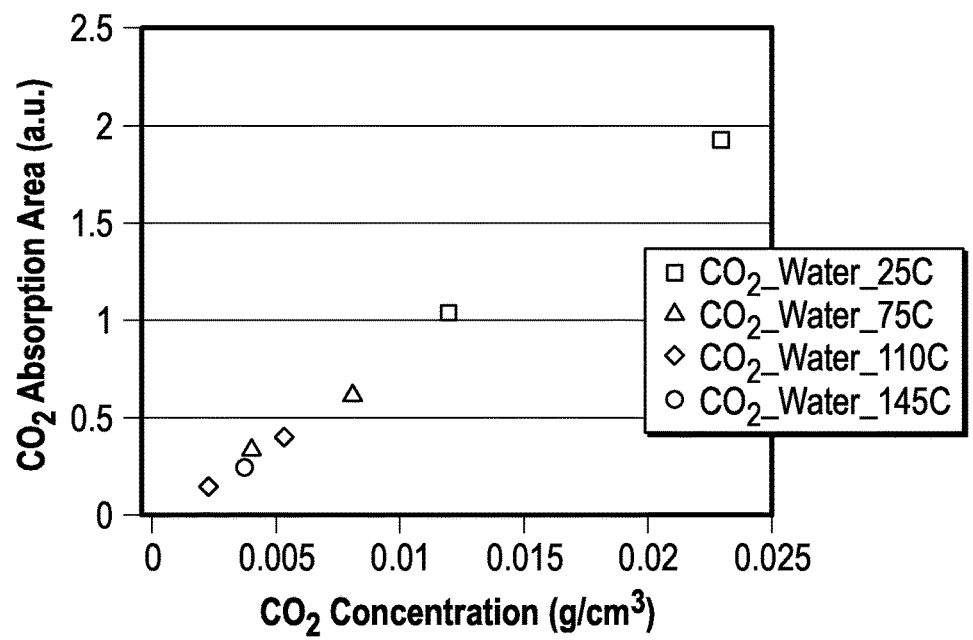

For example, FIG. 15(a) shows an absorbance spectrum for the case where the window 4 is wetted by a water phase. The spectrum is characterised by high absorption by water at 3.00 µm, almost no absorption by oil at 3.45 µm. The $CO_2$ concentration is proportional to the net $CO_2$ absorption, which is the difference between the $CO_2$ channel at 4.27 µm and the reference channel at 4.00 µm. The proportionality constant allowing $CO_2$ concentration in the water phase to be determined from $CO_2$ absorption can be obtained from an experimental plot of $CO_2$ absorbance against dissolved $CO_2$ concentration in water, such as shown in FIG. 15(b).

Figure 16A:
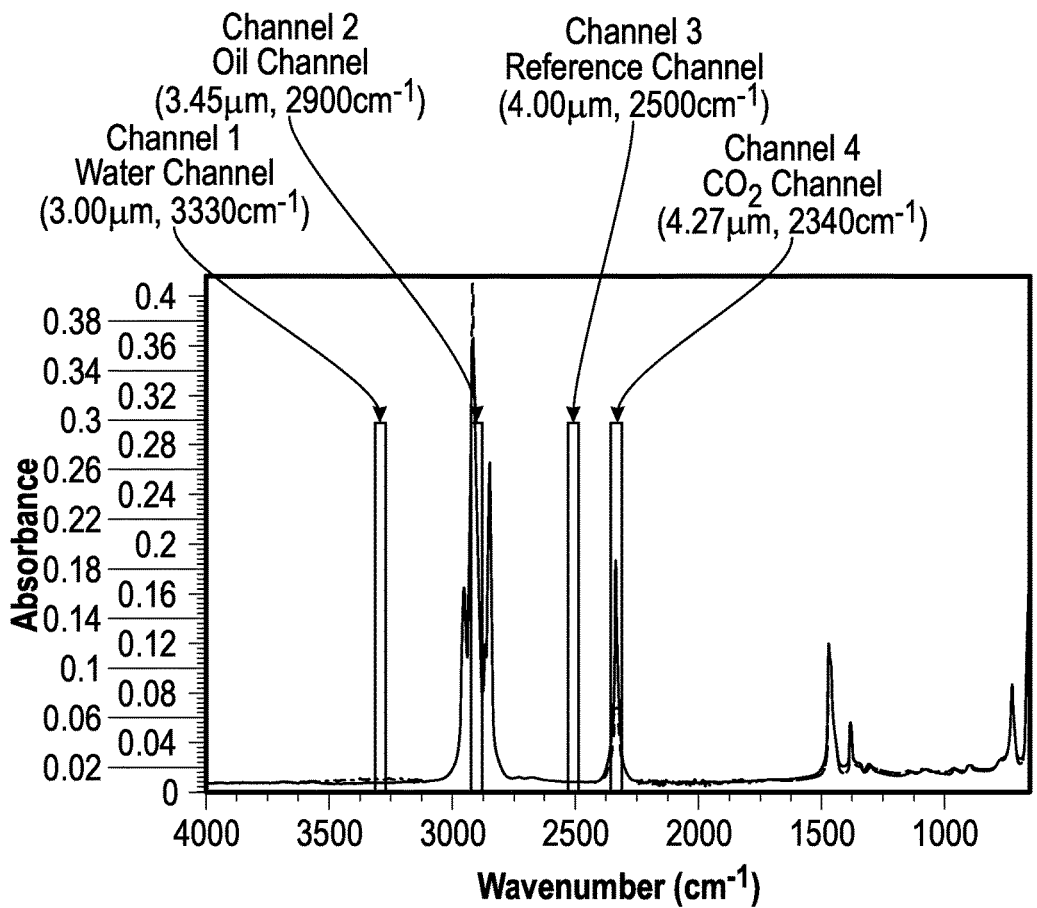
FIG. 16 shows (a) a mid-infrared absorbance spectrum for an oil phase and $CO_2$, and (b) a corresponding plot of absorbance against $CO_2$ concentration for $CO_2$ in oil.
Figure 16B:
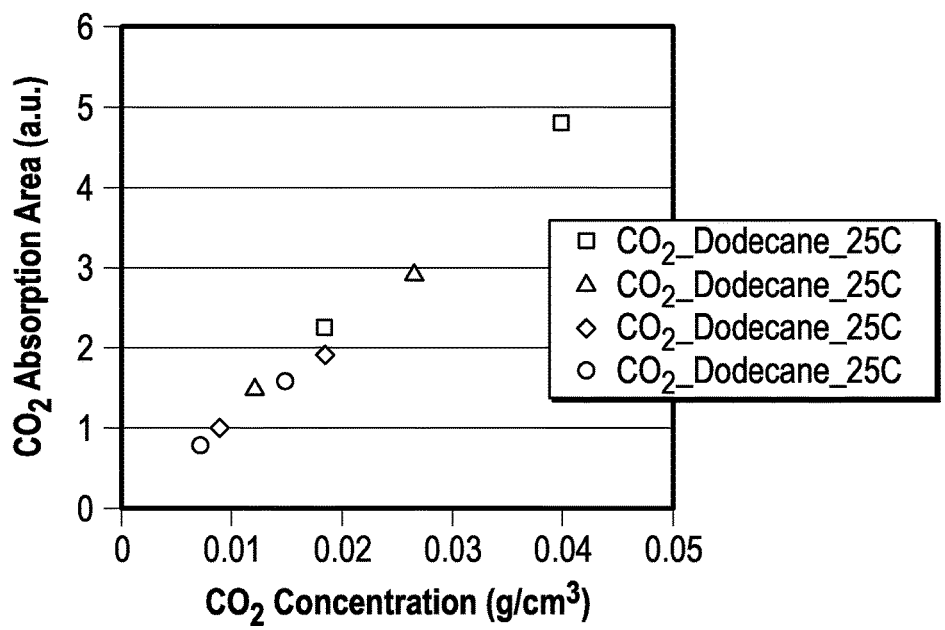

Similarly, FIG. 16(a) shows an absorbance spectrum for the case where the window 4 is wetted by an oil phase. The spectrum is characterised by high absorption by oil at 3.45 um µm almost no absorption by water at 3.00 µm. Again, the $CO_2$ concentration is proportional to the net $CO_2$ absorption, which is the difference between the $CO_2$ channel at 4.27 µm and the reference channel at 4.00 µm. The proportionality constant allowing $CO_2$ concentration in the oil phase to be determined from $CO_2$ absorption can be obtained from an experimental plot of $CO_2$ absorbance against dissolved $CO_2$ concentration in oil, such as shown in FIG. 16(b).

Figure 17:
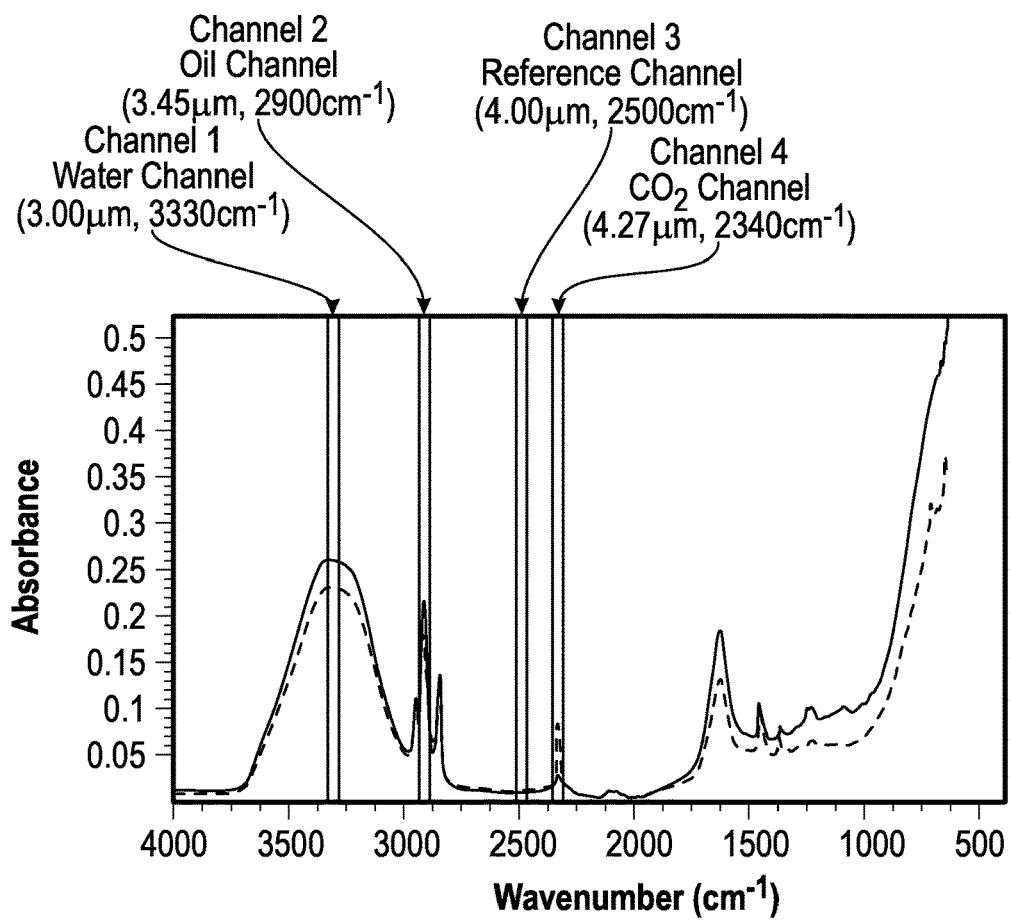
FIG. 17 shows a mid-infrared absorbance spectrum for a water phase, an oil phase and $CO_2$.

Next, FIG. 17 shows an absorbance spectrum for the case where the window 4 is wetted by a mixture of water and oil phases. The spectrum is characterised by absorption by water at 3.00 µm and by oil at 3.45 µm. Again the $CO_2$ concentration is proportional to the net $CO_2$ absorption, which is the difference between the $CO_2$ channel at 4.27 µm and the reference channel at 4.00 µm. However, the proportionality constant is slightly different for water and for oil because their refractive indices, and thus their depths of investigation, are different. Specifically, oil has higher refractive index than water, thus its depth of investigation is deeper and potentially more $CO_2$ is sensed by the sensor in oil than in water. Thus, when the window is wetted by a mixture of both water and oil phase, the mixture proportionality constant is between those of water and oil, but can be calculated from therethem. For example, a simple approach is to use a "lever rule", whereby if the water peak height is X % of its full height and the oil peak height is (100−X) % of its full height, the mixture proportionality constant is the sum of X % of the water proportionality constant and (100−X) % of the oil proportionality constant. More elaborate schemes can be used, but the simple "lever rule" approach works reasonably well because the difference between the water and oil proportionality constants is in any event not great.

Figure 18:
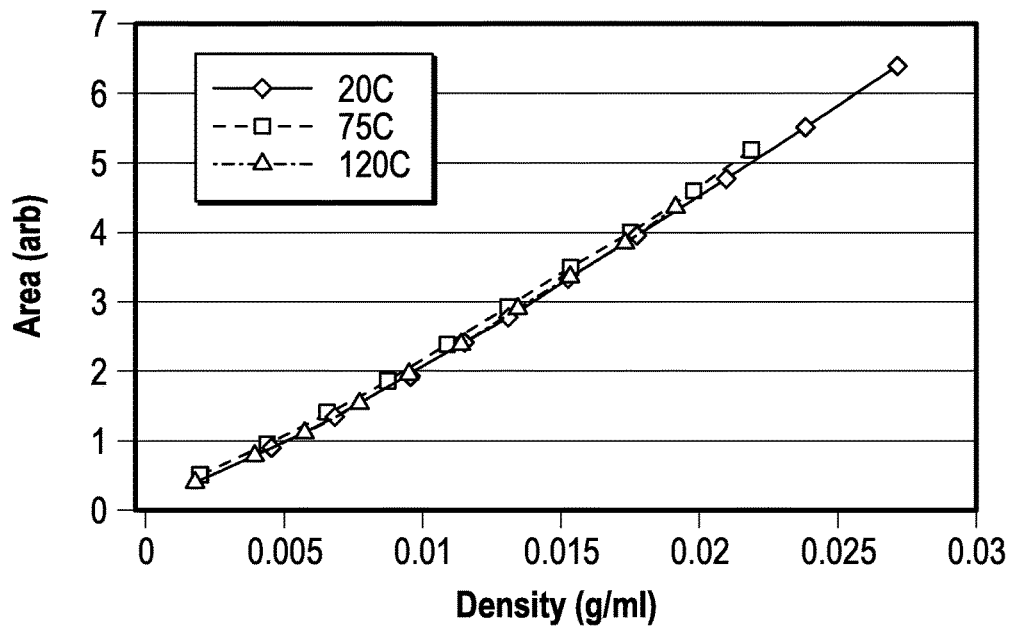
FIG. 18 shows a plot of absorbance against $CO_2$ concentration for $CO_2$ in gas phase.

Under some circumstances, the sensor window 5 may be dry. The spectrum is characterised by almost no absorption by water at 3.00 µm or by oil at 3.45 µm. $CO_2$ concentration is proportional to the net $CO_2$ absorption, which is the difference between the $CO_2$ channel at 4.27 µm and the reference channel at 4.00 µm. The proportionality constant allowing $CO_2$ concentration in the gas phase to be determined from $CO_2$ absorption can be obtained from an experimental plot of $CO_2$ absorbance against $CO_2$ concentration in gas phase, such as shown in FIG. 18.

Monitoring of $CO_2$ concentration can be particularly useful when performed in combination with monitoring of mineral acid concentrations. In particular, the mineral acid sensor can provide a measure of how much acid is being deployed to stimulate a carbonate formation, and the $CO_2$ sensor, by measuring the amount of $CO_2$ produced, can provide a measure of the effectiveness of that acid deployment.

Heater

As mentioned above, the sensor of FIG. 1 may comprise a heater 8 which is operable to locally heat the window 4, thereby cleaning the surface of the window in contact with the fluid.

Cleaning the window in this manner is particularly effective, compared to other techniques such as ultrasonic cleaning or mechanical wiper cleaning.

The window 4 can be formed, for example, of diamond (e.g. by chemical vapour deposition). In some embodiments of the present disclosure, a central (typically undoped) area of the window can be mid-infrared transmissive, while an annular encircling area of the window can be made semiconductive, e.g. by boron doping that part of the window. The heater 8 may comprise a simple electrical power source which sends a current through the window to induce resistive heating of the encircling area. The central area of the window is then heated by thermal conduction from the encircling area. Boron-doping of diamond components is discussed in U.S. Pat. No. 7,407,566, which is incorporated by reference herein for all purposes.

In some embodiments of the present disclosure, the heater 8 may be able to heat the window to at least about 400° C. This is higher than the 374° C. super-critical point for water, where super-critical water is a good cleaner and oxidiser. In embodiments of the present disclosure, it may be unnecessary to keep the window at high temperature for a long time period. In particular, less than a microsecond at peak temperature may be enough for cleaning purposes, with longer periods requiring more power and increasing the risk of overheating of other parts of the sensor.

Pressure Pulse Cleaner

In addition, or as an alternative, to the above heater, cleaning of the window 4 may, in some embodiments of the present disclosure, be performed by providing the sensor with a pressure pulse arrangement. For example, the sensor may be located on a fluid flow line between a pump for the fluid and an exit port from the flow line. With the exit port in a closed position, the fluid pressure can be increased in front of the window to above hydrostatic pressure by the pump. Subsequent of opening the exit port creates a sudden pressure difference that flushes the flowline fluid, e.g. to the borehole. The sudden movement of dense fluid in front of the window dislodges and carries away window contamination. A 1000 psi (6.9 MPa) pressure pulse is generally sufficient in most cases.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions and alterations herein without departing from such scope.

All references referred to above are hereby incorporated by reference.

The invention claimed is:

1. A sensor for monitoring a mineral acid dissolved in a liquid, the sensor comprising:
   an internal reflection window which, in use, is in contact with the liquid;
   a mid-infrared light source configured to direct a beam of mid-infrared radiation into the internal reflection window for attenuated internal reflection at an interface between the internal reflection window and the liquid;
   a first narrow bandpass filter configured to preferentially transmit mid-infrared radiation over a band of wavelengths corresponding to an absorbance peak of the dissolved mineral acid to filter internally reflected mid-infrared radiation received from the internal reflection window and configured such that its band of wavelengths is substantially temperature invariant over temperatures in a range from about 25° C. to about 150° C.;
   an infrared detector configured to detect filtered mid-infrared radiation transmitted through the first narrow bandpass filter; and
   a processor arrangement, operably coupled to the infrared detector and configured to measure an intensity of the detected mid-infrared radiation transmitted through the first narrow bandpass filter and determine an amount of the mineral acid dissolved in the liquid from the measured intensity.

2. The sensor according to claim 1, wherein the first narrow bandpass filter preferentially transmits mid-infrared radiation over a band of wavelengths corresponding to an absorbance peak of about 1050 $cm^{-1}$.

3. The sensor according to claim 1, further comprising
   a second narrow bandpass filter configured to transmit mid-infrared radiation over a band of wavelengths corresponding to a reference portion of the absorbance spectrum of the liquid,
   the or a further infrared detector configured to detect filtered mid-infrared radiation transmitted through the second filter, and
   the processor arrangement configured to measure the reference intensity of the detected mid-infrared radiation transmitted through the second filter and use the measured reference intensity in the determination of the amount of the mineral acid in the fluid.

4. The sensor according to claim 1, wherein the beam of mid-infrared light is pulsed.

5. The sensor according to claim 1, wherein the internal reflection window is a diamond internal reflection window or a sapphire internal reflection window.

6. The sensor according to claim 1, further comprising
   a heater which is-operable to locally heat the internal reflection window, thereby cleaning the surface of the internal reflection window in contact with the liquid.

7. The sensor according to claim 1, further comprising
   a pressure pulse arrangement which is operable to produce a pressure pulse in the fluid at the internal reflection window, thereby cleaning the surface of the internal reflection window in contact with the fluid.

8. The sensor according to claim 1 which is configured for use downhole.

9. Use of the sensor of claim 1 to determine an amount of a mineral acid dissolved in a liquid.

10. A method of monitoring a mineral acid dissolved in a liquid, the method comprising:
    providing the sensor of claim 1 such that the internal reflection window is in direct contact with the liquid; and operating the sensor to determine an amount of the mineral acid dissolved in the liquid.

11. A method of stimulating production from a well, the method comprising:
injecting a liquid containing dissolved mineral acid into the well to stimulate production from a carbonate formation;
providing the sensor of claim 1 such that the internal reflection window is in direct contact with the liquid; and
operating the sensor to determine the amount of mineral acid deployed into the formation.

12. The method of claim 11, further comprising:
providing a further sensor for monitoring $CO_2$ in a fluid, the further sensor including:
a further internal reflection window which, in use, is in direct contact with a fluid;
a further mid-infrared light source configured to direct a beam of mid-infrared radiation into the further internal reflection window for attenuated internal reflection at an interface between the further internal reflection window and the fluid;
three further first narrow bandpass filters configured to preferentially transmit mid-infrared radiation over bands of wavelengths corresponding to respective absorbance peaks of water, oil and $CO_2$ to filter internally reflected mid-infrared radiation received from the internal reflection window;
one or more further infrared detector(s) which detect filtered mid-infrared radiation transmitted through the further first narrow bandpass filters; and
a further processor arrangement, operably coupled to the infrared detector(s), configured to measure the intensity of the detected mid-infrared radiation transmitted through the first narrow bandpass filters and determine an amount of $CO_2$ in the fluid from the measured intensity notwithstanding whether the fluid contacting the further internal reflection window is a liquid water-based phase, a liquid oil-based phase, a mixture of liquid water and liquid oil-based phases, or a gas phase; and
operating the further sensor to determine an amount of $CO_2$ in the fluid produced by the formation.

13. A method for monitoring a mineral acid dissolved in a liquid, the method comprising:
directing a beam of mid-infrared radiation into an internal reflection window contacting the liquid;
passing an attenuated internal reflection from the internal reflection window of the mid-infrared radiation through a narrow bandpass filter to produce a filtered output beam of mid-infrared radiation, wherein the narrow bandpass filter is configured to preferentially transmit mid-infrared radiation over a band of wavelengths corresponding to an absorbance peak of the dissolved mineral acid and is configured such that its band of wavelengths is substantially temperature invariant over temperatures in a range from about 25° C. to about 150° C.;
measuring an intensity of the filtered output beam; and
determining an amount of the mineral acid dissolved in the liquid from the measured intensity.

14. The method according to claim 13, wherein the narrow bandpass filter is configured to preferentially transmit mid-infrared radiation over a band of wavelengths corresponding to an absorbance peak of 1050 $cm^{-1}$.

15. The method according to claim 13, further comprising:
passing the attenuated internal reflection from the internal reflection window through a second narrow bandpass filter configured to transmit mid-infrared radiation over a band of wavelengths corresponding to a reference portion of the absorbance spectrum of the liquid to produce a reference output; and
measuring an intensity of the reference output,
wherein: determining an amount of the mineral acid dissolved in the liquid from the measured intensity comprises determining an amount of the mineral acid dissolved in the liquid from the measured intensity and the reference intensity.

16. The method according to claim 13, wherein the beam of mid-infrared light is pulsed.

17. The method according to claim 13, further comprising:
rapidly heating the internal reflection window to remove contaminants from the internal reflection window.

18. The method according to claim 13, further comprising:
applying a pressure pulse to the liquid to remove contaminants from the internal reflection window.

19. The method according to claim 13, further comprising:
determining an amount of $CO_2$ in the liquid.

20. A method of stimulating production from a well, the method comprising:
injecting a liquid containing dissolved mineral acid into the well to stimulate production from a carbonate formation;
providing a sensor for monitoring the dissolved mineral acid, the sensor comprising:
an internal reflection window which, in use, is in contact with the liquid;
a mid-infrared light source configured to direct a beam of mid-infrared radiation into the internal reflection window for attenuated internal reflection at an interface between the internal reflection window and the liquid;
a first narrow bandpass filter configured to preferentially transmit mid-infrared radiation over a band of wavelengths corresponding to an absorbance peak of the dissolved mineral acid to filter internally reflected mid-infrared radiation received from the internal reflection window;
an infrared detector configured to detect filtered mid-infrared radiation transmitted through the first narrow bandpass filter; and
a processor arrangement, operably coupled to the infrared detector and configured to measure an intensity of the detected mid-infrared radiation transmitted through the first narrow bandpass filter and determine an amount of the mineral acid dissolved in the liquid from the measured intensity;
wherein the internal reflection window is in direct contact with the liquid;
operating the sensor to determine the amount of mineral acid deployed into the formation;
providing a further sensor for monitoring $CO_2$ in a fluid, the further sensor comprising:
a further internal reflection window which, in use, is in direct contact with a fluid;
a further mid-infrared light source configured to direct a beam of mid-infrared radiation into the further internal reflection window for attenuated internal reflection at an interface between the further internal reflection window and the fluid;

three further first narrow bandpass filters configured to preferentially transmit mid-infrared radiation over bands of wavelengths corresponding to respective absorbance peaks of water, oil and $CO_2$ to filter internally reflected mid-infrared radiation received from the internal reflection window;

one or more further infrared detector(s) which detect filtered mid-infrared radiation transmitted through the further first narrow bandpass filters; and a further processor arrangement, operably coupled to the infrared detector(s), configured to measure the intensity of the detected mid-infrared radiation transmitted through the first narrow bandpass filters and determine an amount of $CO_2$ in the fluid from the measured intensity notwithstanding whether the fluid contacting the further internal reflection window is a liquid water-based phase, a liquid oil-based phase, a mixture of liquid water and liquid oil-based phases, or a gas phase; and operating the further sensor to determine an amount of $CO_2$ in the fluid produced by the formation.

* * * * *